United States Patent
Mandula et al.

(10) Patent No.: US 11,766,256 B2
(45) Date of Patent: Sep. 26, 2023

(54) SURGICAL STAPLING DEVICE WITH PARALLEL JAW CLOSURE

(71) Applicant: Covidien LP, Mansfield, MA (US)

(72) Inventors: Rajanikanth Mandula, Hyderabad (IN); Roanit Fernandes, Hyderabad (IN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/528,674

(22) Filed: Nov. 17, 2021

(65) Prior Publication Data
US 2022/0071628 A1     Mar. 10, 2022

Related U.S. Application Data

(62) Division of application No. 16/895,164, filed on Jun. 8, 2020, now Pat. No. 11,191,538.

(51) Int. Cl.
*A61B 17/068* (2006.01)
*A61B 17/072* (2006.01)

(52) U.S. Cl.
CPC ........ *A61B 17/0686* (2013.01); *A61B 17/072* (2013.01); *A61B 2017/0725* (2013.01); *A61B 2017/07257* (2013.01); *A61B 2017/07271* (2013.01); *A61B 2017/07285* (2013.01)

(58) Field of Classification Search
CPC ............ A61B 17/0684; A61B 17/0686; A61B 17/072; A61B 17/07207; A61B 2017/0725; A61B 2017/07257; A61B 2017/07271; A61B 17/2813; A61B 17/2816; A61B 2017/2936; A61B 2017/2939; A61B 2017/2944
USPC ........................................... 227/175.1, 181.1
See application file for complete search history.

(56) References Cited

U.S. PATENT DOCUMENTS

| | | | |
|---|---|---|---|
| 3,499,591 | A | 3/1970 | Green |
| 3,777,538 | A | 12/1973 | Weatherly et al. |
| 3,882,854 | A | 5/1975 | Hulka et al. |
| 4,027,510 | A | 6/1977 | Hiltebrandt |
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

European Search Report dated Mar. 7, 2022, issued in corresponding EP Appln. No. 21175789, 8 pages.

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

A surgical stapling device includes a tool assembly having an anvil, a cartridge assembly movable in relation to the anvil between open and clamped positions, a drive member, and a biasing mechanism or member. The biasing mechanism or member is configured to urge the cartridge assembly in relation to the anvil assembly to its fully open position to provide access to tissue during a surgical procedure.

20 Claims, 16 Drawing Sheets

(56) References Cited

U.S. PATENT DOCUMENTS

| | | |
|---|---|---|
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |

(56) References Cited

U.S. PATENT DOCUMENTS

| | | | |
|---|---|---|---|
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A * | 5/1997 | Schulze | A61B 17/07207 227/176.1 |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A | 9/1997 | Bishop et al. | |
| 5,662,666 A | 9/1997 | Onuki et al. | |
| 5,665,085 A | 9/1997 | Nardella | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Billner et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,690,269 A | 11/1997 | Bolanos et al. | |
| 5,690,675 A | 11/1997 | Sawyer et al. | |
| 5,692,668 A | 12/1997 | Schulze et al. | |
| 5,697,542 A * | 12/1997 | Knodel | A61B 17/07207 227/19 |
| 5,702,409 A | 12/1997 | Rayburn et al. | |
| 5,704,534 A | 1/1998 | Huitema et al. | |
| 5,706,997 A | 1/1998 | Green et al. | |
| 5,709,334 A | 1/1998 | Sorrentino et al. | |
| 5,711,472 A | 1/1998 | Bryan | |
| 5,713,505 A | 2/1998 | Huitema | |
| 5,715,988 A | 2/1998 | Palmer | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,728,110 A | 3/1998 | Vidal et al. | |
| 5,732,806 A | 3/1998 | Foshee et al. | |
| 5,735,848 A | 4/1998 | Fates et al. | |
| 5,743,456 A | 4/1998 | Jones et al. | |
| 5,749,893 A | 5/1998 | Vidal et al. | |
| 5,752,644 A | 5/1998 | Bolanos et al. | |
| 5,762,255 A | 6/1998 | Chrisman et al. | |
| 5,762,256 A | 6/1998 | Mastri et al. | |
| 5,769,303 A | 6/1998 | Knodel et al. | |
| 5,769,892 A | 6/1998 | Kingwell | |
| 5,772,099 A | 6/1998 | Gravener | |
| 5,772,673 A | 6/1998 | Cuny et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,782,834 A | 7/1998 | Lucey et al. | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,810,811 A | 9/1998 | Yates et al. | |
| 5,810,855 A | 9/1998 | Rayburn et al. | |
| 5,814,055 A * | 9/1998 | Knodel | A61B 17/07207 606/139 |
| 5,814,057 A | 9/1998 | Oi et al. | |
| 5,816,471 A | 10/1998 | Plyley et al. | |
| 5,817,109 A | 10/1998 | McGarry et al. | |
| 5,820,009 A | 10/1998 | Melling et al. | |
| 5,823,066 A | 10/1998 | Huitema et al. | |
| 5,826,776 A | 10/1998 | Schulze et al. | |
| 5,829,662 A | 11/1998 | Allen et al. | |
| 5,833,695 A | 11/1998 | Yoon | |
| 5,836,147 A | 11/1998 | Schnipke | |
| 5,862,972 A | 1/1999 | Green et al. | |
| 5,865,361 A | 2/1999 | Milliman et al. | |
| 5,871,135 A | 2/1999 | Williamson IV et al. | |
| 5,873,873 A | 2/1999 | Smith et al. | |
| 5,878,938 A | 3/1999 | Bittner et al. | |
| 5,893,506 A | 4/1999 | Powell | |
| 5,894,979 A | 4/1999 | Powell | |
| 5,897,562 A | 4/1999 | Bolanos et al. | |
| 5,901,895 A | 5/1999 | Heaton et al. | |
| 5,911,352 A | 6/1999 | Racenet et al. | |
| 5,911,353 A | 6/1999 | Bolanos et al. | |
| 5,918,791 A | 7/1999 | Sorrentino et al. | |
| 5,919,198 A | 7/1999 | Graves, Jr. et al. | |
| 5,922,001 A | 7/1999 | Yoon | |
| 5,931,847 A | 8/1999 | Billner et al. | |
| 5,941,442 A | 8/1999 | Geiste et al. | |
| 5,954,259 A | 9/1999 | Viola et al. | |
| 5,964,774 A | 10/1999 | McKean et al. | |
| 5,980,510 A | 11/1999 | Tsonton et al. | |
| 5,988,479 A | 11/1999 | Palmer | |
| 6,004,335 A | 12/1999 | Vaitekunas et al. | |
| 6,010,054 A | 1/2000 | Johnson et al. | |
| 6,032,849 A | 3/2000 | Mastri et al. | |
| 6,045,560 A | 4/2000 | McKean et al. | |
| 6,063,097 A | 5/2000 | Oi et al. | |
| 6,079,606 A | 6/2000 | Milliman et al. | |
| 6,099,551 A | 8/2000 | Gabbay | |
| 6,109,500 A | 8/2000 | Alli et al. | |
| 6,131,789 A | 10/2000 | Schulze et al. | |
| 6,131,790 A | 10/2000 | Piraka | |
| 6,155,473 A | 12/2000 | Tompkins et al. | |
| 6,197,017 B1 | 3/2001 | Brock et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,279,809 B1 | 8/2001 | Nicolo | |
| 6,315,183 B1 | 11/2001 | Piraka | |
| 6,315,184 B1 | 11/2001 | Whitman | |
| 6,325,810 B1 | 12/2001 | Hamilton et al. | |
| 6,330,965 B1 | 12/2001 | Milliman et al. | |
| 6,391,038 B2 | 5/2002 | Vargas et al. | |
| 6,398,797 B2 | 6/2002 | Bombard et al. | |
| 6,436,097 B1 | 8/2002 | Nardella | |
| 6,439,446 B1 | 8/2002 | Perry et al. | |
| 6,443,973 B1 | 9/2002 | Whitman | |
| 6,478,804 B2 | 11/2002 | Vargas et al. | |
| 6,488,196 B1 | 12/2002 | Fenton, Jr. | |
| 6,503,257 B2 | 1/2003 | Grant et al. | |
| 6,505,768 B2 | 1/2003 | Whitman | |
| 6,544,274 B2 | 4/2003 | Danitz et al. | |
| 6,554,844 B2 | 4/2003 | Lee et al. | |
| 6,565,554 B1 | 5/2003 | Niemeyer | |
| 6,587,750 B2 | 7/2003 | Gerbi et al. | |
| 6,592,597 B2 | 7/2003 | Grant et al. | |
| 6,594,552 B1 | 7/2003 | Nowlin et al. | |
| 6,602,252 B2 | 8/2003 | Mollenauer | |
| 6,619,529 B2 | 9/2003 | Green et al. | |
| D480,808 S | 10/2003 | Wells et al. | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,681,978 B2 | 1/2004 | Geiste et al. | |
| 6,698,643 B2 | 3/2004 | Whitman | |
| 6,716,232 B1 | 4/2004 | Vidal et al. | |
| 6,722,552 B2 | 4/2004 | Fenton, Jr. | |

(56) References Cited

U.S. PATENT DOCUMENTS

| | | |
|---|---|---|
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |

(56) References Cited

U.S. PATENT DOCUMENTS

| | | |
|---|---|---|
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 * | 2/2010 | Vidal .................. A61B 17/282 227/180.1 |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |

(56) References Cited

U.S. PATENT DOCUMENTS

| | | |
|---|---|---|
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 3,011,551 A1 | 9/2011 | Marczyk et al. |
| 8,011,550 B2 | 9/2011 | Aranyi et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |

(56) References Cited

U.S. PATENT DOCUMENTS

| | | |
|---|---|---|
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |

(56) References Cited

U.S. PATENT DOCUMENTS

| | | |
|---|---|---|
| 8,616,427 B2 | 12/2013 | Viola |
| 8,616,430 B2 | 12/2013 | Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,827,136 B2 * | 9/2014 | Hessler ............ A61B 17/07207 227/176.1 |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |

(56) References Cited

U.S. PATENT DOCUMENTS

| | | |
|---|---|---|
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,839,428 B2 * | 12/2017 | Baxter, III ....... A61B 17/07207 |
| 10,695,058 B2 | 6/2020 | Lytle, IV et al. |
| 11,191,538 B1 | 12/2021 | Mandula et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0051669 A1 | 3/2010 | Milliman |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 * | 11/2011 | Knodel ............ A61B 17/07207 227/176.1 |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |

(56) References Cited

U.S. PATENT DOCUMENTS

| | | |
|---|---|---|
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Meaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |

(56) References Cited

U.S. PATENT DOCUMENTS

| | | |
|---|---|---|
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2018/0263644 A1* | 9/2018 | Batchelor ............ A61B 17/282 |
| 2018/0317914 A1 | 11/2018 | Badawi |
| 2019/0090893 A1* | 3/2019 | Hirai ............. A61B 17/320092 |
| 2019/0298352 A1 | 10/2019 | Shelton, IV et al. |
| 2019/0321062 A1* | 10/2019 | Williams ............. A61B 17/122 |
| 2021/0267596 A1* | 9/2021 | Fanelli .................... A61B 34/30 |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 20150191887 A1 | 12/2015 |
| WO | WO-2017199411 A1 * | 11/2017 ........... A61B 17/068 |

\* cited by examiner

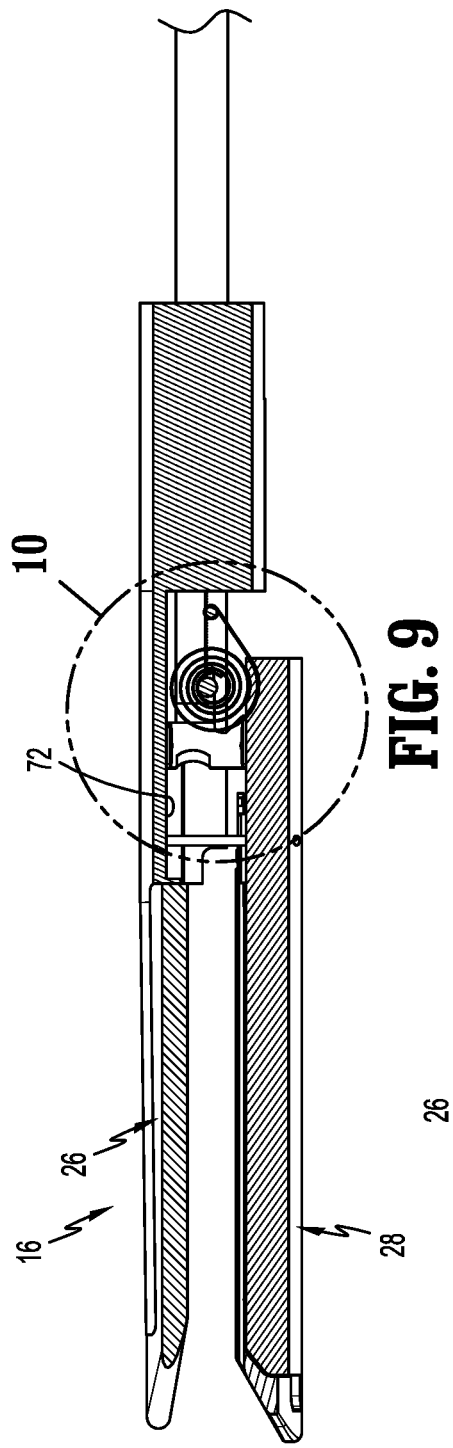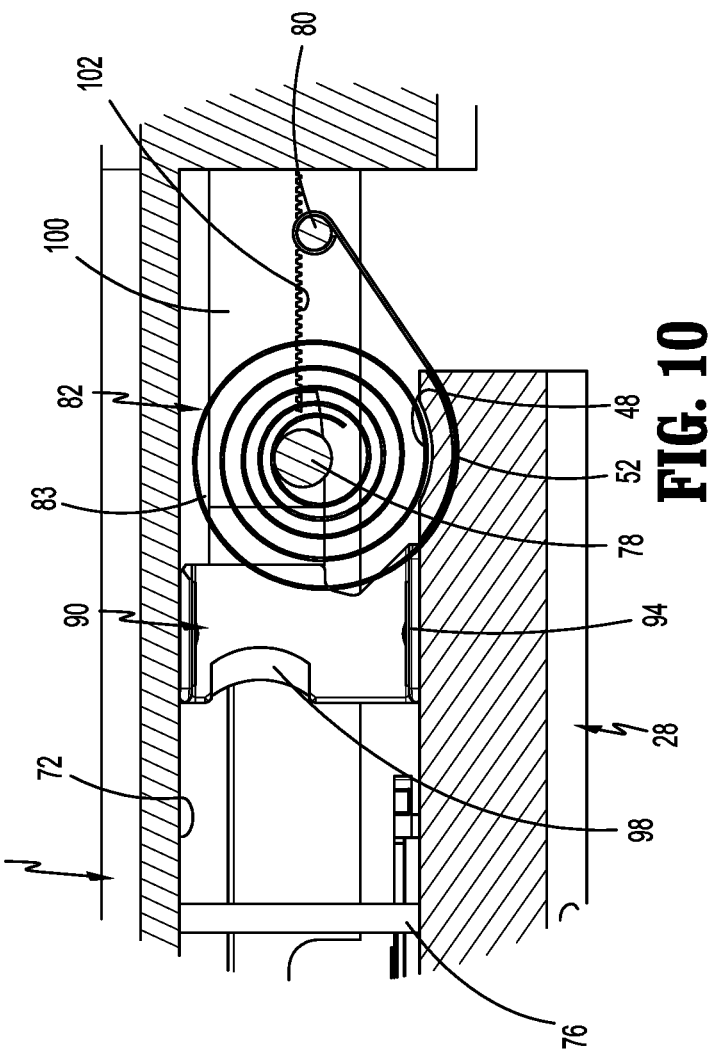

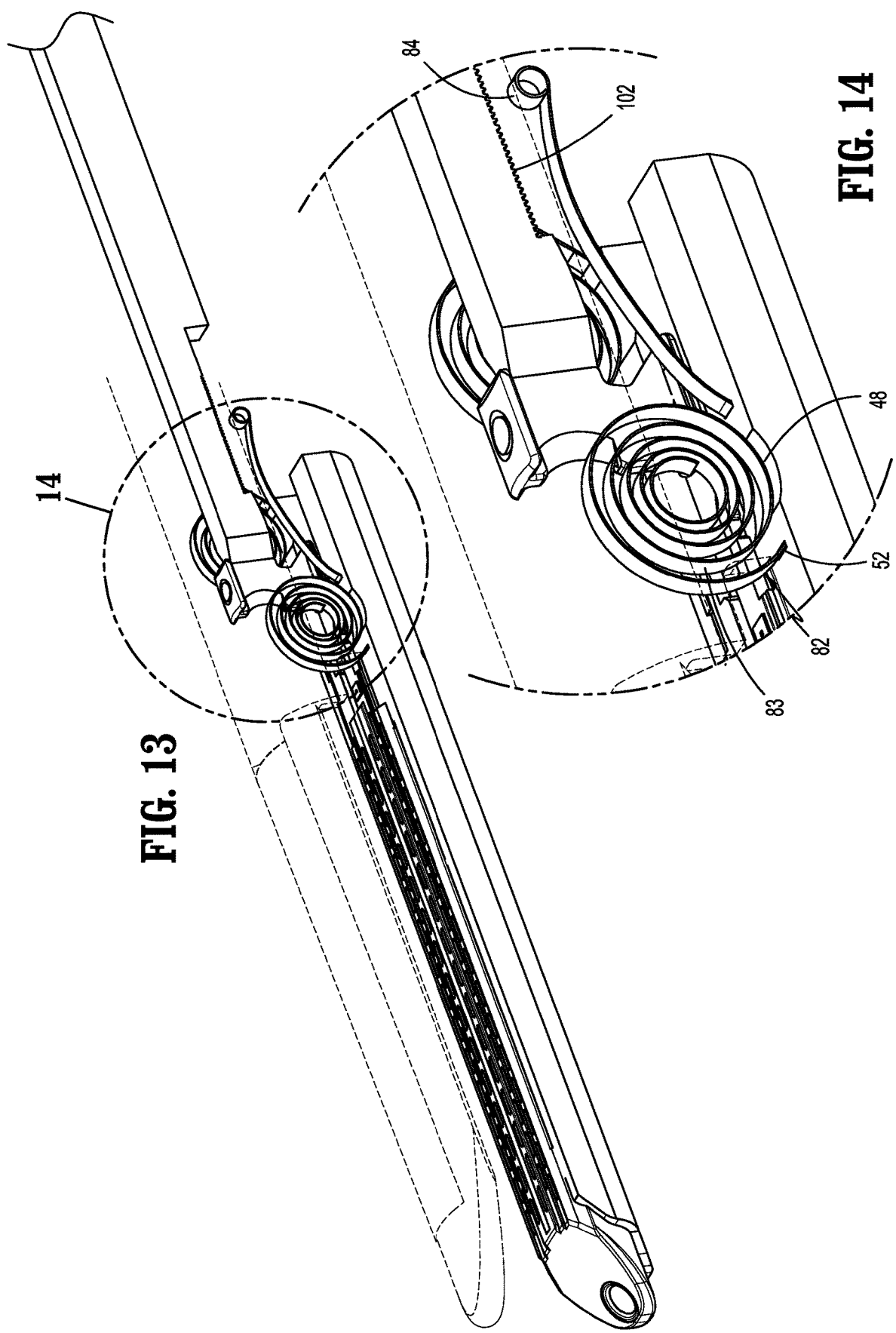

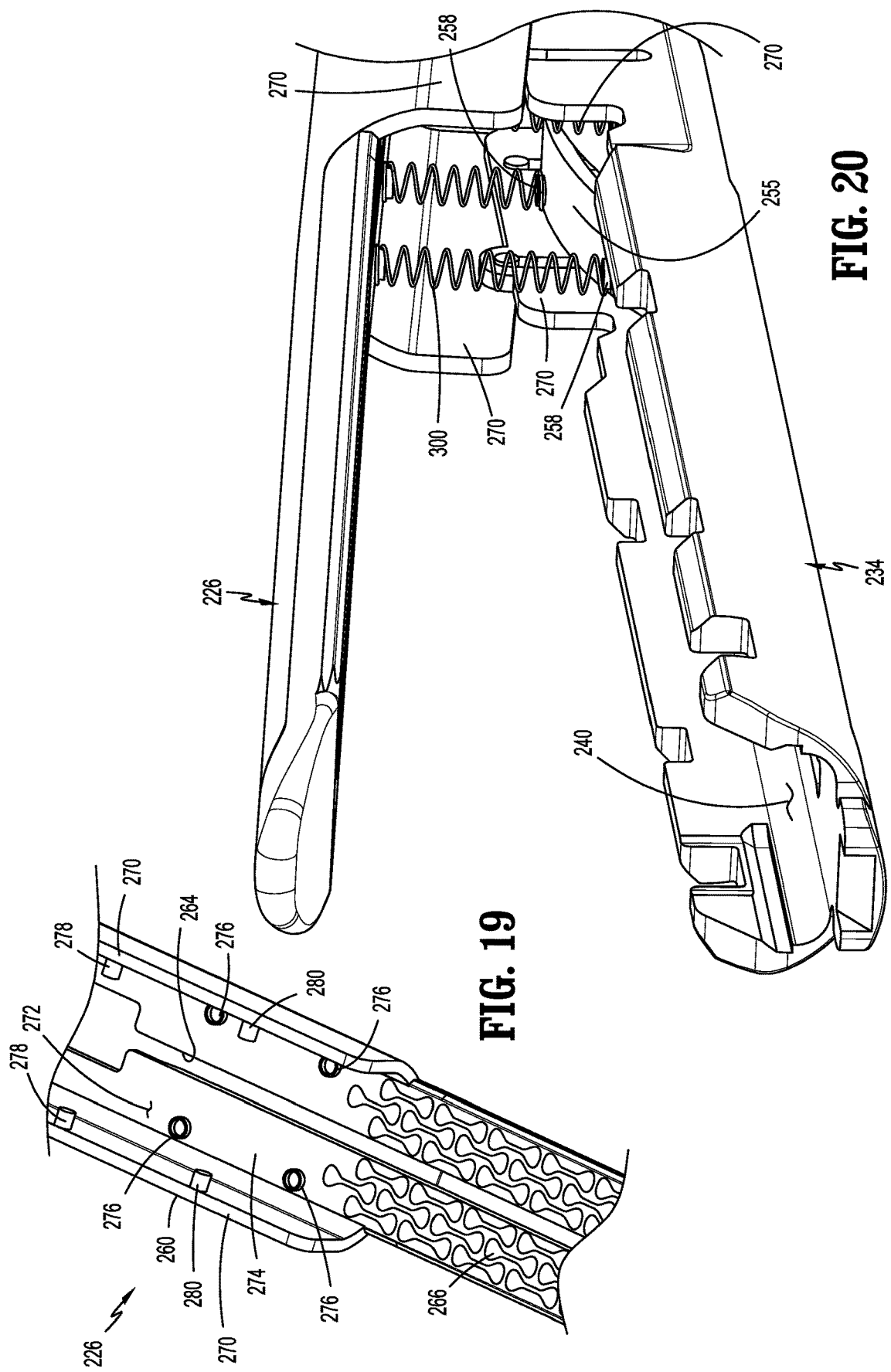

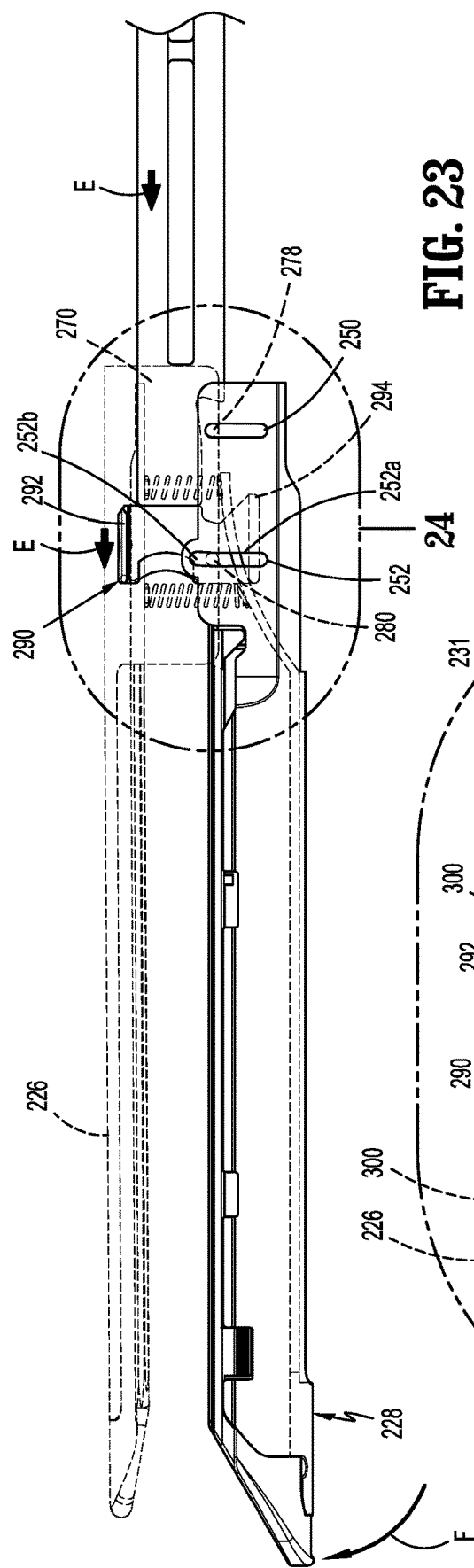
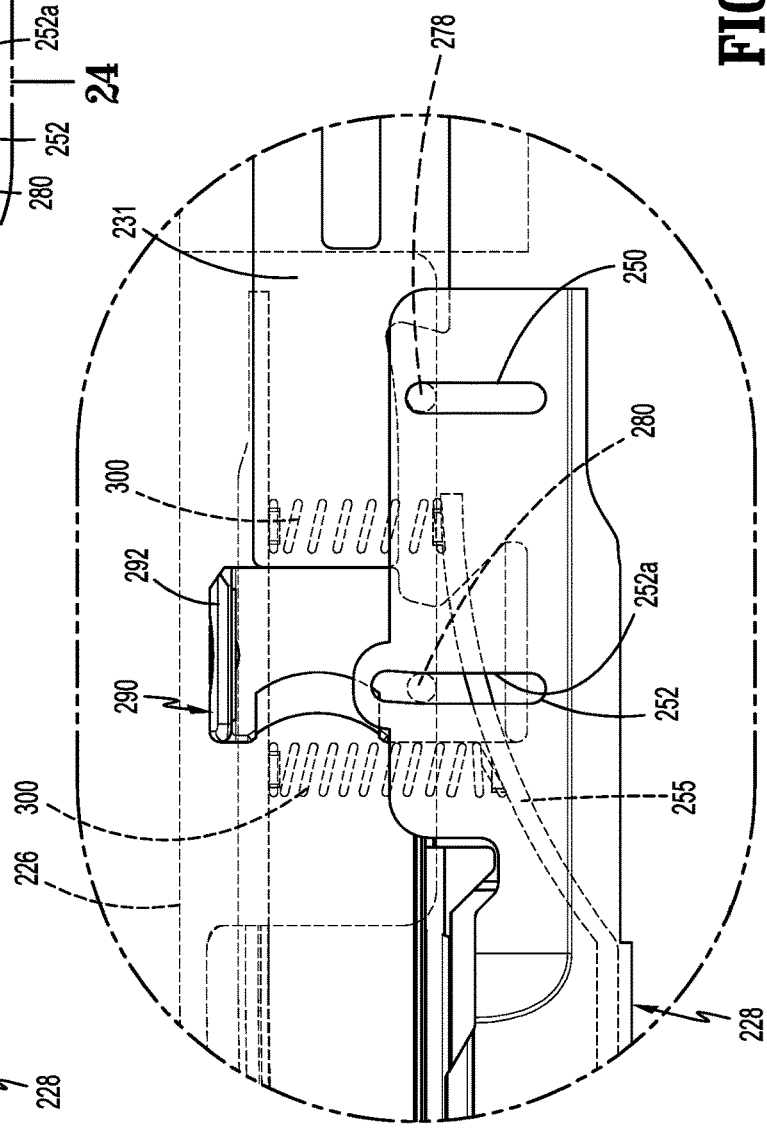

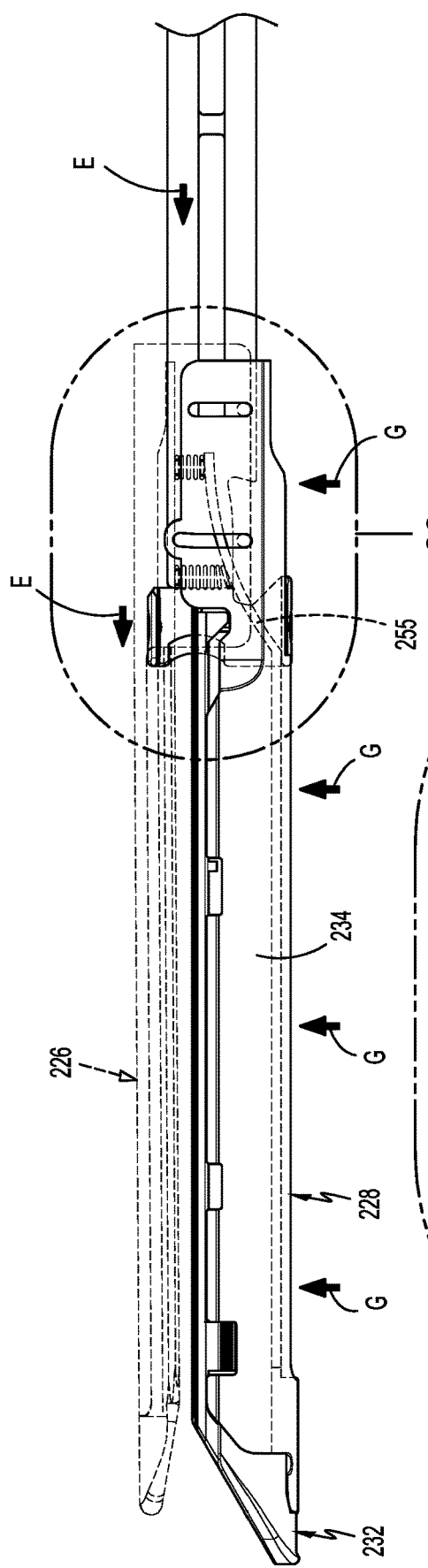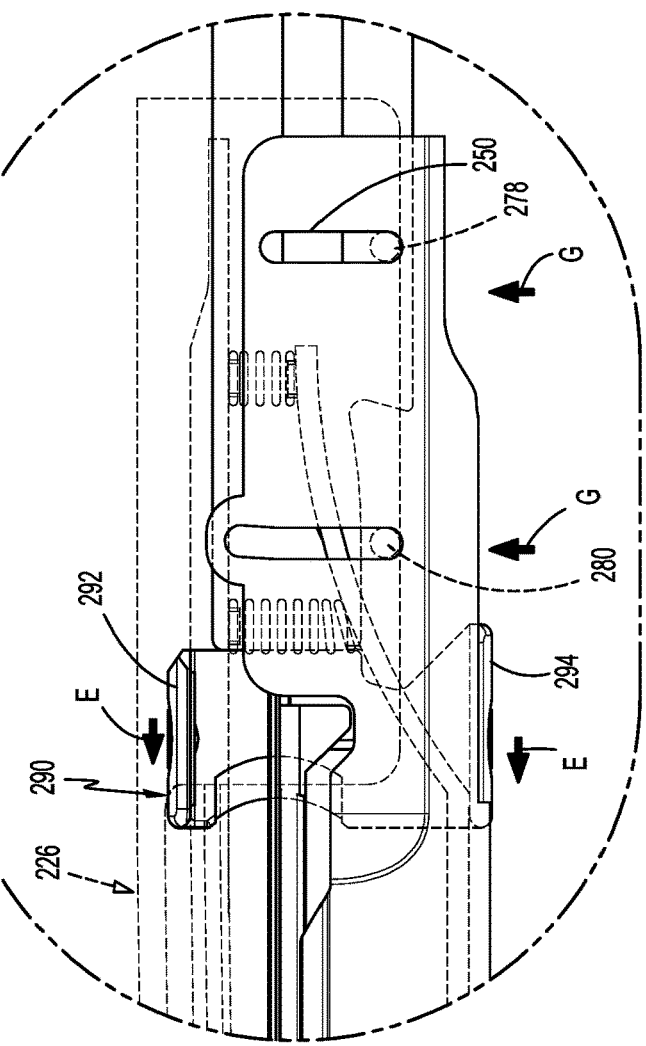

SURGICAL STAPLING DEVICE WITH PARALLEL JAW CLOSURE

CROSS-REFERENCE TO RELATED APPLICATIONS

This application is a Divisional Application of U.S. patent application Ser. No. 16/895,164, filed on Jun. 8, 2020, the entire disclosure of which is incorporated by reference herein.

FIELD

This technology is generally related to stapling devices and, more particularly, to surgical stapling devices with parallel jaw closure.

BACKGROUND

Surgical stapling devices for simultaneously cutting and stapling tissue are known in the art and are commonly used during surgical procedures to reduce the time required to perform the surgical procedure and to facilitate endoscopic access to a surgical site. Performing a surgical procedure endoscopically reduces the amount of trauma inflicted on a patient during the surgical procedure to minimize patient discomfort and reduce patient recovery times.

Typically, endoscopic stapling devices include a tool assembly having a first jaw, and a second jaw that can pivot in relation to the first jaw between an open or spaced position and a closed or clamped position. One of the first or second jaws supports a cartridge assembly that includes a plurality of staples and the other of the first or second jaws supports an anvil assembly that includes an anvil having staple deforming pockets that receive and form legs of the staples when the staples are ejected from the cartridge assembly.

In surgical procedures that require a stapling device including a tool assembly having jaws of an extended length, e.g., bariatric procedures and procedures involving the bowel or lungs, the surgical site is confined by the anatomy of the patient. This confinement may make it difficult to move the jaws of the tool assembly to a fully open position to receive and treat tissue.

SUMMARY

In aspects, this disclosure generally relates to a surgical stapling device including an anvil, a cartridge assembly movable in relation to the anvil between open and clamped positions, a drive member, and a biasing mechanism or member. The biasing mechanism or member is configured to urge the cartridge assembly in relation to the anvil assembly to its fully open position to provide access to tissue during a surgical procedure.

One aspect of this disclosure is directed to a tool assembly including an anvil, a cartridge assembly, a biasing mechanism, and a drive member. The anvil includes a body having a proximal portion and a distal portion. The body defines a central knife slot and includes a staple forming surface. The proximal portion of the body includes spaced side walls that define an anvil cavity. At least one of the side walls supports a boss that extends into the anvil cavity. The cartridge assembly includes a channel member and a staple cartridge. The channel member includes side walls and a base wall that define a channel cavity that receives the staple cartridge. At least one of the side walls of the channel member defines a slot that extends through a portion of the respective side wall. The cartridge assembly is movable in relation to the anvil to move the tool assembly from the open position to the clamped position. The biasing mechanism includes at least one spiral spring and a roller including a toothed portion. The roller is rotatably supported between the side walls of the anvil. The at least one spiral spring includes a coil portion and a first end. The coil portion of the at least one spiral spring is supported on the boss on the at least one side wall of the anvil in a position between the anvil and the channel member. The at least one spiral spring extends through the slot in the at least one side wall of the channel member. The first end of the at least one spiral spring is connected to the roller. The drive member includes a beam portion and a working end. The drive member is movable in relation to the anvil and the cartridge assembly from a retracted position to an advanced position to actuate the tool assembly. The beam portion includes a toothed rack that is engaged with the toothed portion of the roller such that movement of the drive member from its retracted position towards its advanced position causes rotation of the roller to wind the at least one spiral spring about the roller and move the tool assembly from the open position to the clamped position.

Another aspect of the disclosure is directed to a surgical stapling device including a handle assembly, an elongate body, and a tool assembly. The handle assembly includes a stationary handle. The elongate body has a proximal portion coupled to the handle assembly and a distal portion. The tool assembly is supported on the distal portion of the elongate body and includes an anvil, a cartridge assembly, a biasing mechanism, and a drive member. The anvil includes a body having a proximal portion and a distal portion. The body defines a central knife slot and includes a staple forming surface. The proximal portion of the body includes spaced side walls that define an anvil cavity. At least one of the side walls supports a boss that extends into the anvil cavity. The cartridge assembly includes a channel member and a staple cartridge. The channel member includes side walls and a base wall that define a channel cavity that receives the staple cartridge. At least one of the side walls of the channel member defines a slot that extends through a portion of the respective side wall. The cartridge assembly is movable in relation to the anvil to move the tool assembly from the open position to the clamped position. The biasing mechanism includes at least one spiral spring and a roller including a toothed portion. The roller is rotatably supported between the side walls of the anvil. The at least one spiral spring includes a coil portion and a first end. The coil portion of the at least one spiral spring is supported on the boss on the at least one side wall of the anvil in a position between the anvil and the channel member. The at least one spiral spring extends through the slot in the at least one side wall of the channel member. The first end of the at least one spiral spring is connected to the roller. The drive member includes a beam portion and a working end. The drive member is movable in relation to the anvil and the cartridge assembly from a retracted position to an advanced position to actuate the tool assembly. The beam portion includes a toothed rack that is engaged with the toothed portion of the roller such that movement of the drive member from its retracted position towards its advanced position causes rotation of the roller to wind the at least one spiral spring about the roller and move the tool assembly from the open position to the clamped position.

In aspects of the disclosure, the at least one spiral spring includes two spiral springs.

In some aspects of the disclosure, the toothed portion of the roller is centrally located on the roller and one of the two spiral springs is positioned on each side of the toothed portion of the roller.

In certain aspects of the disclosure, each of the side walls of the channel member defines a circular concavity and the coil of each of the two spiral springs is received within a respective one of the circular concavities on the side wall of the channel member.

In aspects of the disclosure, the anvil defines a longitudinal axis and supports spaced pins, and each of the spaced pins defines a longitudinal axis that is perpendicular to the longitudinal axis of the anvil.

In some aspects of the disclosure, each of the side walls of the channel member defines a bore, and each of the spaced pins of the anvil is received within one of the bores to maintain the anvil and the cartridge assembly in parallel alignment with each other as the tool assembly is moved between the open position and the clamped position.

In certain aspects of the disclosure, the working end of the drive member includes a first beam, a second beam, and a vertical strut interconnecting the first and second beams.

In aspects of the disclosure, the first beam engages the anvil and the second beam engages the cartridge assembly to define a maximum tissue gap between the anvil and the cartridge assembly during firing of the tool assembly.

Another aspect of this disclosure is directed to a tool assembly including an anvil, a cartridge assembly, and a drive member. The anvil includes a body having a proximal portion and a distal portion. The body defines a central knife slot and includes a staple forming surface. The proximal portion of the body includes spaced side walls that define an anvil cavity. Each of the side walls supports a distal pivot member and a proximal pivot member. The distal pivot member is longitudinally spaced from the proximal pivot member. The distal and proximal pivot members extend from the respective side walls of the channel member into the anvil cavity. The cartridge assembly defines a longitudinal axis and includes a channel member and a staple cartridge. The channel member includes side walls and a base wall that define a channel cavity that receives the staple cartridge. Each of the side walls of the channel member has a proximal portion that defines first and second slots. The first and second slots define axes that are substantially perpendicular to the longitudinal axis of the cartridge assembly. The first slots are longitudinally spaced from the second slots. Each of the first slots receives a respective one of the distal pivot members and each of the second slots receives a respective one of the proximal pivot members. The cartridge assembly is movable in relation to the anvil to move the tool assembly from its open position to its clamped position. The drive member includes a beam portion and a working end. The drive member is movable in relation to the anvil and the cartridge assembly from a retracted position to an intermediate position and subsequently to a clamped position to move the cartridge assembly in relation to the anvil from the open position to the clamped position. The first and second slots are configured such that that movement of the drive member from the retracted position to the intermediate position pivots the cartridge assembly in relation to the anvil into parallel alignment with the anvil and movement of the drive member from its intermediate position to its clamped position moves the cartridge assembly in relation to the anvil to the clamped position while maintaining the cartridge assembly in parallel relation to the anvil.

In aspects of the disclosure, the first slots include an angled portion that allows the cartridge assembly to pivot in relation to the anvil as the drive member moves from its retracted position towards the intermediate position.

In some aspects of the disclosure, biasing members are supported between the proximal portion of the anvil and the proximal portion of the channel member, the biasing members urging the cartridge assembly in relation to the anvil towards its clamped position.

In certain aspects of the disclosure, the channel member supports a ramp and the working end of the drive member includes a first beam, a second beam, and a vertical strut interconnecting the first and second beams.

In aspects of the disclosure, the first beam engages the anvil and the second beam engages the ramp of the cartridge assembly as the drive member is moved from its retracted position to its clamped position to move the cartridge assembly in relation to the anvil from its open position to its clamped position.

In some aspects of the disclosure, the biasing members include coil springs that are supported between the ramp of the cartridge assembly and the anvil.

Other features of the disclosure will be appreciated from the following description.

BRIEF DESCRIPTION OF DRAWINGS

Various aspects of the disclosure are described herein below with reference to the drawings, wherein:

FIG. 9 is a cross-sectional view taken along section line 8-8 of FIG. 2;

FIG. 10 is an enlarged view of the indicated area of detail shown in FIG. 9;

FIG. 13 is a side perspective view of the tool assembly shown in FIG. 11 in an open position;

FIG. 14 is an enlarged view of the indicated area of detail shown in FIG. 13;

FIG. 19 is a perspective view from below of a proximal portion of the anvil of the tool assembly shown in FIG. 16;

FIG. 20 is a perspective view from a distal end of the tool assembly shown in FIG. 15 with a staple cartridge removed from a cartridge assembly of the tool assembly and the tool assembly in the open position;

FIG. 23 is a side perspective view of the tool assembly shown in FIG. 15 in the an intermediate position between the open and clamped positions with the anvil shown in phantom;

FIG. 24 is an enlarged view of the indicated area of detail shown in FIG. 23;

FIG. 25 is a side perspective view of the tool assembly shown in FIG. 15 in the clamped position with the anvil shown in phantom; and FIG. 26 is an enlarged view of the indicated area of detail shown in FIG. 25.

DETAILED DESCRIPTION

Figure 1:
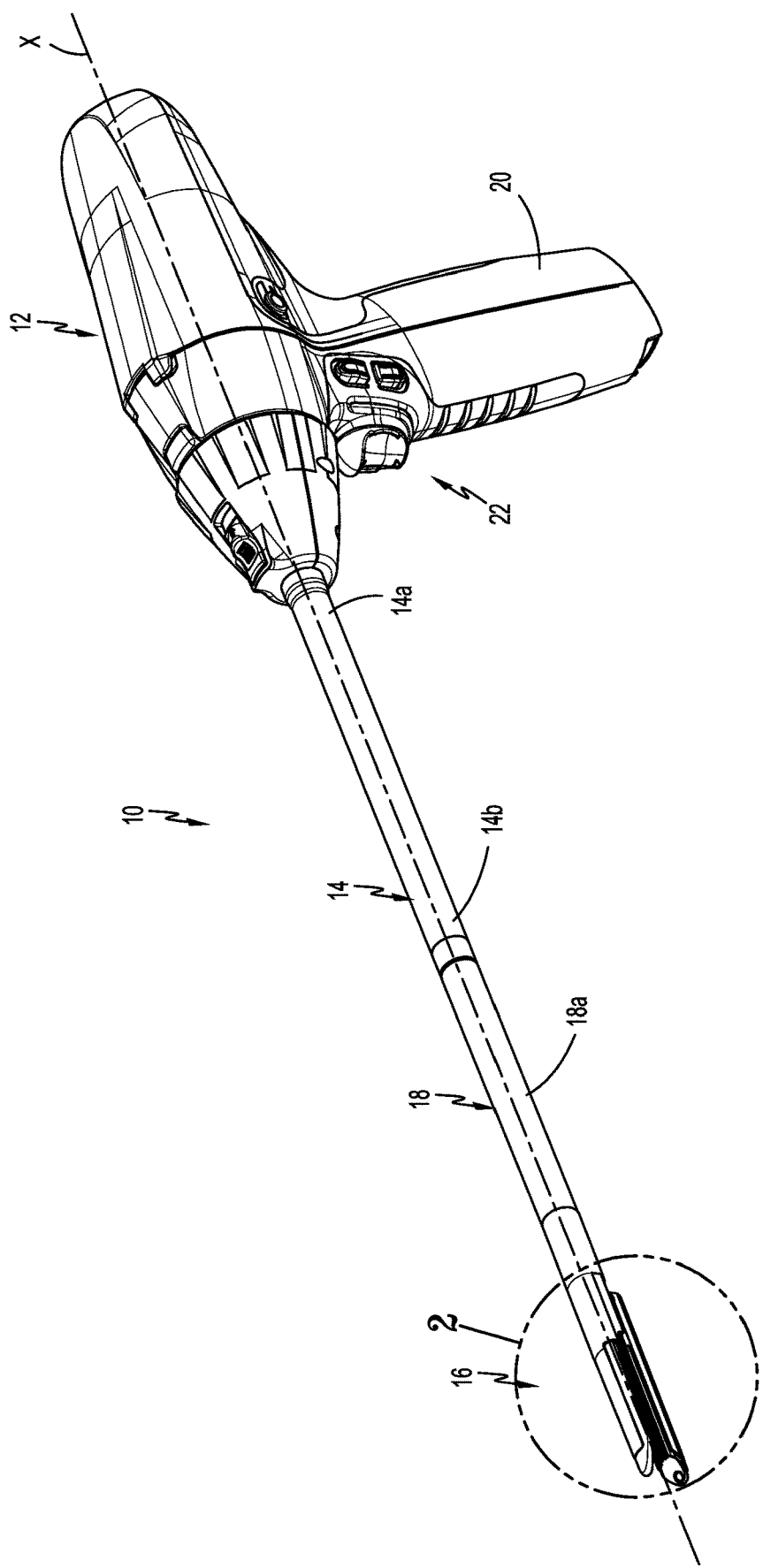
FIG. 1 is a perspective view of exemplary aspects of a surgical stapling device according to aspects of the disclosure.

The disclosed surgical stapling device will now be described in detail with reference to the drawings in which like reference numerals designate identical or corresponding elements in each of the several views. However, it is to be understood that aspects of the disclosure described herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through a small diameter incision or cannula. Further, the term "clinician" is used generally to refer to medical personnel including doctors, nurses, and support personnel. As used herein, the term "substantially parallel" includes true parallel as well as 10 degrees in either direction.

FIG. 1 illustrates exemplary aspects of the disclosed surgical stapling device shown generally as stapling device 10. Stapling device 10 includes a powered handle assembly 12, an elongate body 14, and a tool assembly 16. The elongate body 14 defines a longitudinal axis "X" and includes a proximal portion 14a supported on the handle assembly 12 and a distal portion 14b that supports the tool assembly 16. In some aspects of the disclosure, the tool assembly 16 forms part of a reload assembly 18 that includes a proximal body portion 18a that is releasably coupled to the distal portion 14b of the elongate body 14 of the stapling device 10. The proximal body portion 18a includes a distal portion that supports the tool assembly 16. Although not shown, the tool assembly 16 can be coupled to the proximal body portion 18a by a pivot member that facilitates articulation of the tool assembly 16 about an axis transverse to the longitudinal axis "X" of the elongate body 14. In alternate aspects of the disclosure, the tool assembly 16 is fixedly secured to the distal portion 14b of the elongate body 14. For a description of exemplary aspects of the tool assembly, see, e.g., U.S. Pat. No. 6,241,139 ("the '139 patent").

The handle assembly 12 of the stapling device 10 includes a stationary handle 20 and actuation buttons 22 that can be depressed to actuate the tool assembly 16, e.g., approximate the tool assembly 16, articulate the tool assembly 16, fire staples, etc. In aspects of the disclosure, batteries (not shown) are supported in the stationary handle 20 to power the handle assembly 12. It is envisioned that the stapling device 10 need not be powered but can also include a manually powered handle assembly such as described in the '139 patent.

Figure 2:
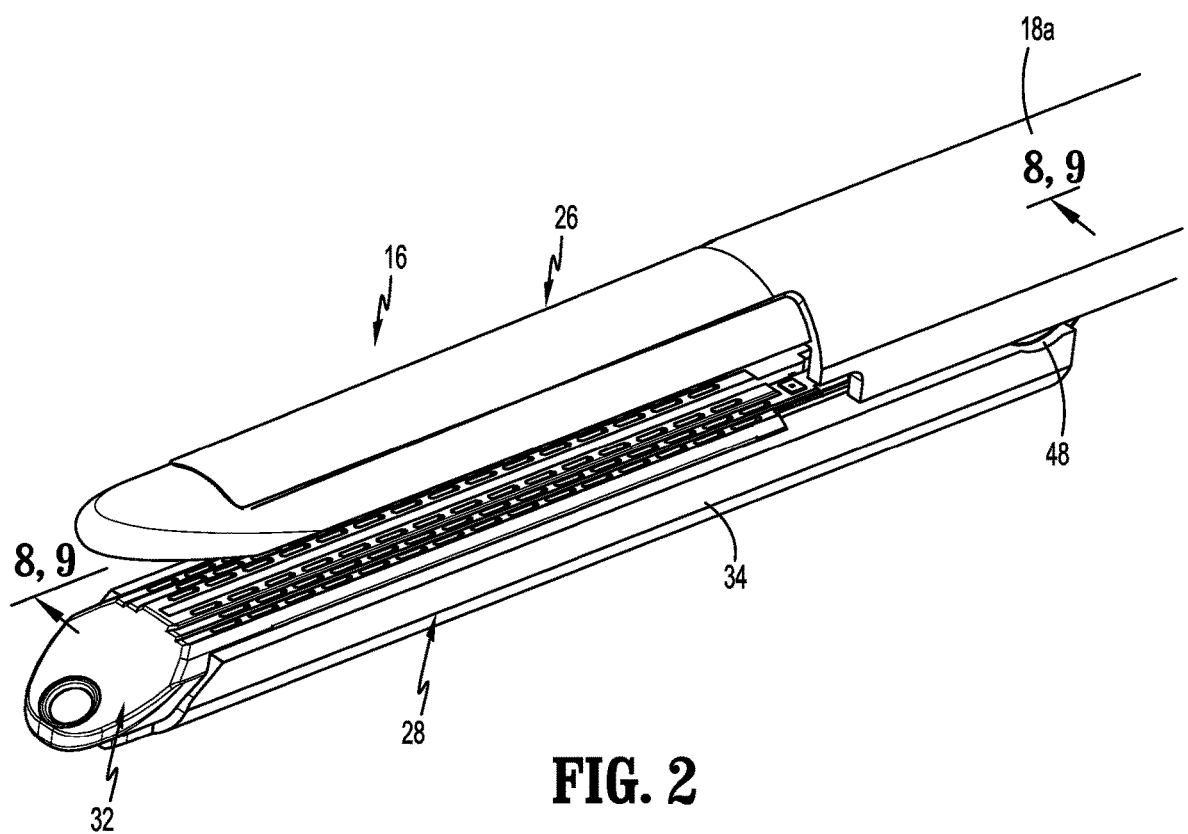
FIG. 2 is an enlarged view of the indicated area of detail shown in FIG. 1.
Figure 3:
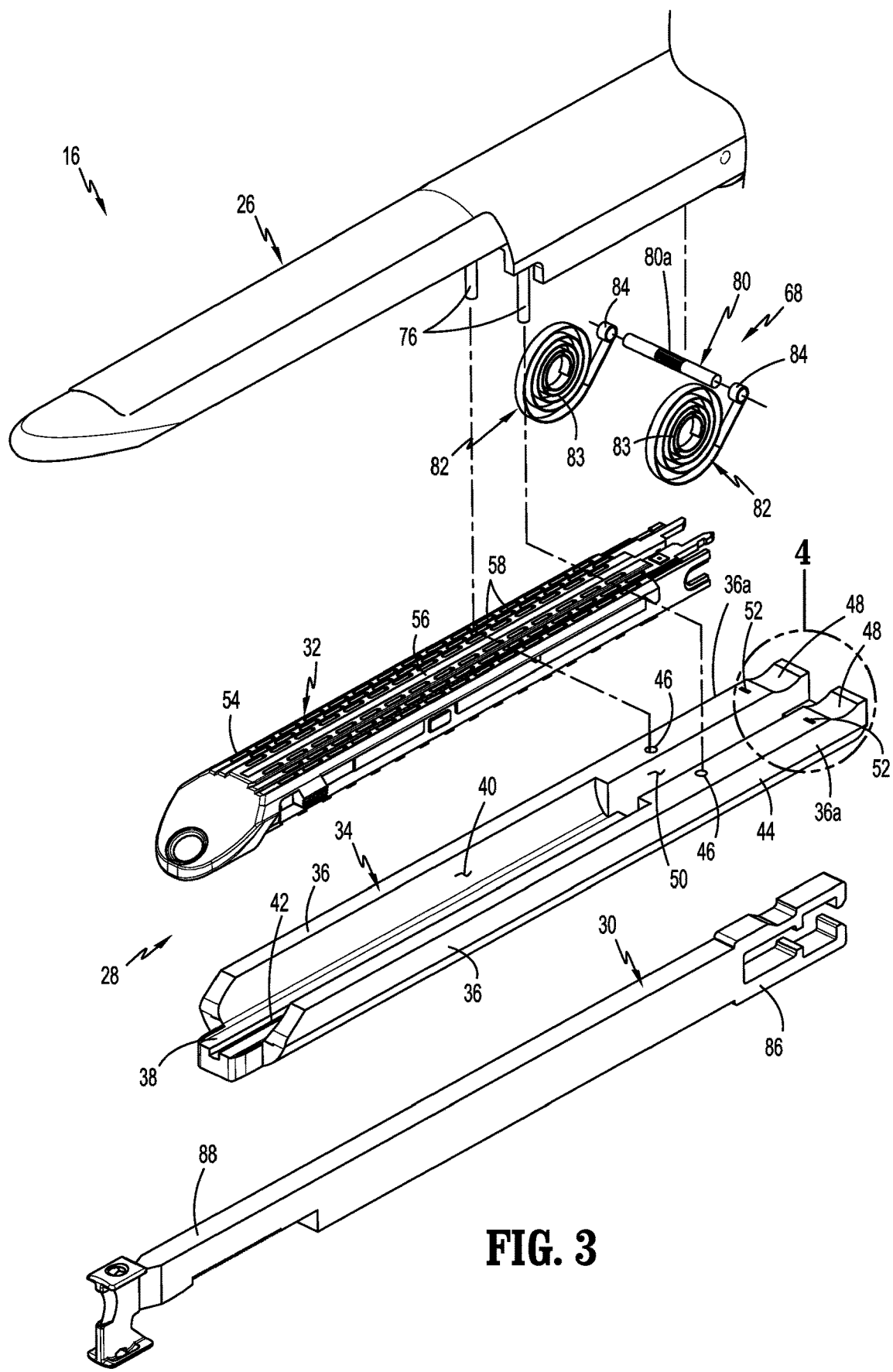
FIG. 3 is a side perspective exploded view of the tool assembly shown in FIG. 2.
Figure 4:
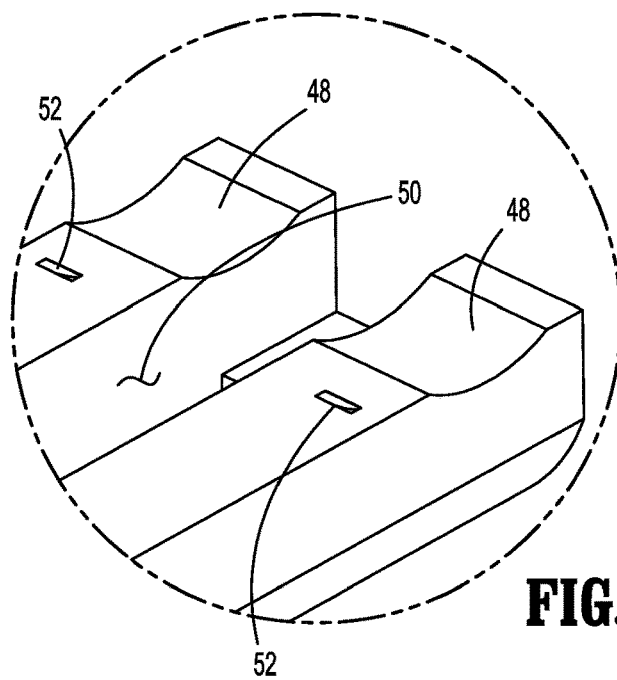
FIG. 4 is an enlarged view of the indicated area of detail shown in FIG. 3.
Figure 11:
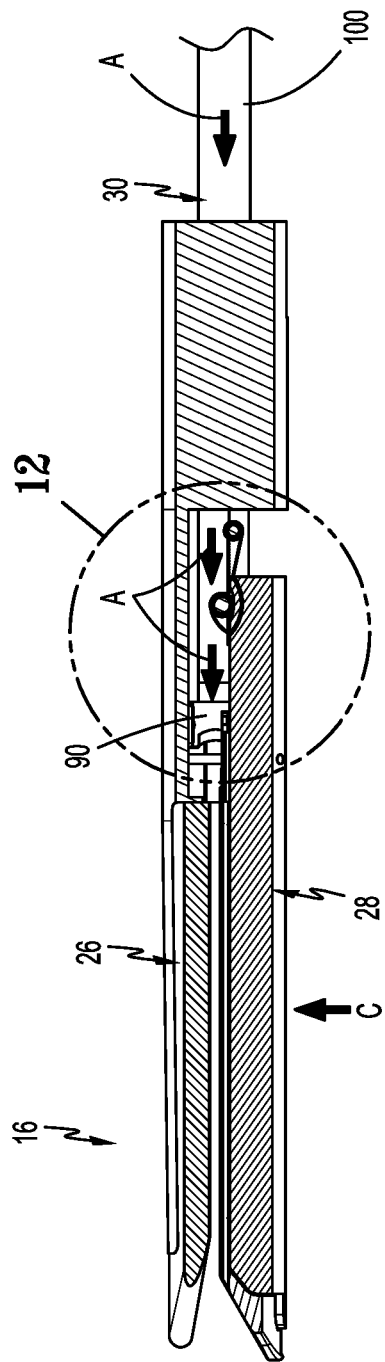
FIG. 11 is a cross-sectional view taken through the tool assembly of the stapling device of FIG. 1 as the tool assembly is moved to a clamped position.

FIGS. 2-4 illustrate the tool assembly 16 of the stapling device 10 in an open position. The tool assembly 16 includes an anvil 26, a cartridge assembly 28, and a drive member 30. The anvil 26 is fixedly secured to a distal end of the proximal body portion 18a of the reload assembly 18 (or to the distal end of the elongate body 14). The cartridge assembly 28 is supported on the anvil 26 for movement between an open position (FIG. 1) and a clamped position (FIG. 11) and includes a staple cartridge 32 and a channel member 34. The channel member 34 includes side walls 36 and a base wall 38 that define a channel cavity 40 that receives the staple cartridge 32. The base wall 38 defines a knife slot 42 that extends through the channel member 34 along most of its length and includes a closed proximal and distal end. The knife slot 42 receives a portion of the drive member 30 to facilitate movement of the drive member 30 in relation to the anvil 26 and cartridge assembly 28 between retracted and advanced positions.

Figure 8:
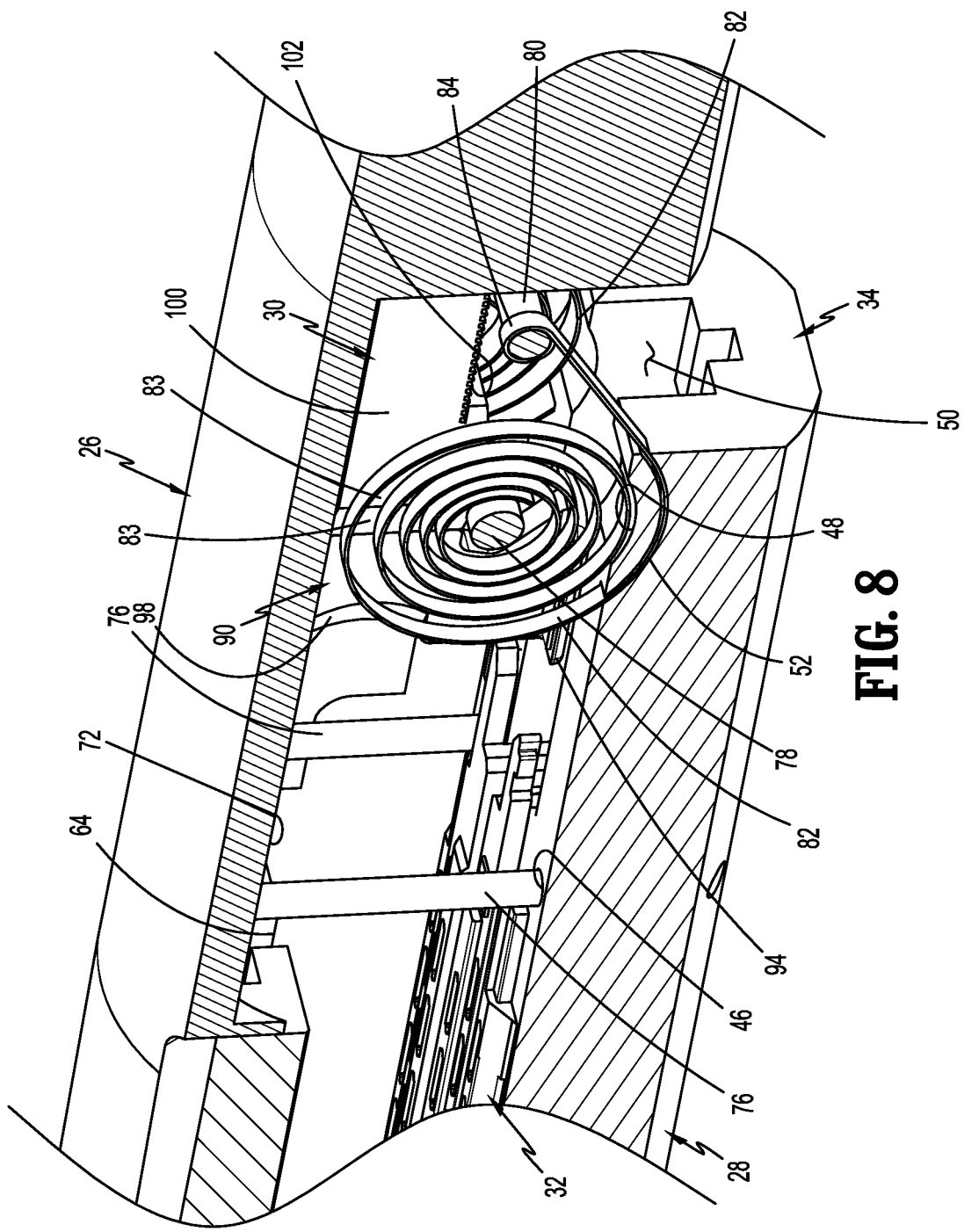
FIG. 8 is a cross-sectional view taken along section line 8-8 of FIG. 2.

The channel member 34 has a proximal portion including a base 44 that is defined by a proximal portion 36a (FIG. 3) of the side walls 36 of the channel member 34. I aspects of the disclosure, the width of the proximal portion 36a of the side walls 36 in the base 44 of the channel member 34 is thicker than the width of the side walls 36 in a distal portion of the channel member 34. Each of the proximal portions 36a of the side walls 36 in the base 44 includes an upper surface (as viewed in FIG. 3) that defines a bore 46 and a circular concavity 48. The bores 46 extend along an axis that is substantially perpendicular to a longitudinal axis of the cartridge assembly 28. The proximal portions 36a of the side walls 36 are spaced from each other to define a channel 50 that communicates with the channel cavity 40 and receives the drive member 30 when the drive member 30 is in its retracted position. Each of the proximal portions 36a of the side walls 36 of the channel member 34 also defines a circular slot 52 that extends through the side wall 36a from an upper surface of the side wall 36 of the channel member 34 to the proximal end of the side wall 36 of the channel member 34 (FIG. 8).

The staple cartridge 32 is received within the channel cavity 40 and includes a cartridge body 54 that defines a central knife slot 56 and rows of staple pockets 58 on each side of the central knife slot 56. It is envisioned that two or more rows of staple pockets can be provided on each side of the central knife slot 56. It is also envisioned that the staple pockets 58 need not be aligned in rows but rather a variety of different arrays of staple pockets 58 can be defined on each side of the central knife slot 56. Each of the staple pockets 58 receives a staple and a pusher (not shown). For a more detailed description of the staple cartridge 32 including staples and pushers, see the '139 Patent.

Figure 5:
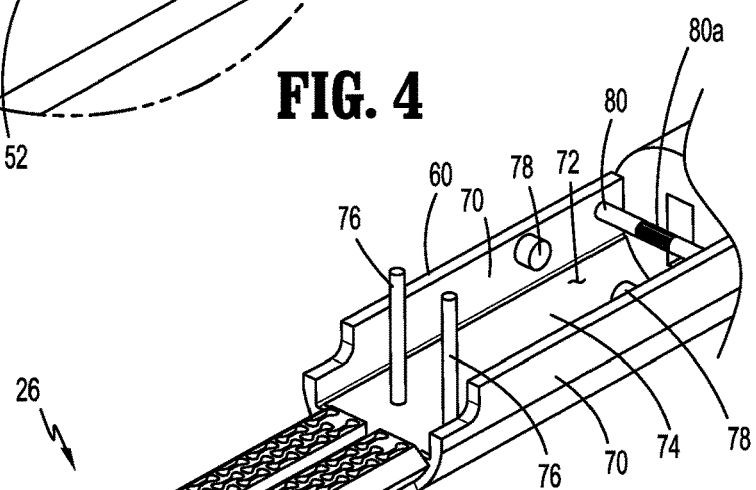
FIG. 5 is a side perspective view of the anvil of the tool assembly shown in FIG. 3.

FIGS. 3 and 5 illustrate the anvil 26 of the stapling device 10 (FIG. 1) which includes a proximal portion 60 and a distal portion 62. The distal portion 62 of the anvil 26 defines a central knife slot 64 and includes a staple forming surface 66. The central knife slot 64 extends from the staple forming surface 66 and communicates with an internal channel (not shown) defined within the anvil 26. The central knife slot 64 and the internal channel (not shown) within the anvil 26 receive a portion of the drive member 30 as the drive member 30 is moved between its retracted and advanced positions.

The proximal portion 60 of the anvil 26 includes a pair of spaced side walls 70 that defines an anvil cavity 72 that receives the base 44 of the channel member 34 when the tool assembly is in its clamped position. The anvil cavity 72 is defined in part by a base wall 74 of the anvil 26 which supports two spaced pins 76 that extend upwardly from the base wall 74 (as viewed in FIG. 5) within the anvil cavity 72 towards the cartridge assembly 28. The pins 76 define an axis that is substantially perpendicular to a longitudinal axis of the anvil 26 and are received within the bores 46 formed in the proximal portions 36a of the side walls 36 of the channel member 34. The side walls 70 also support bosses 78 that extend from the side walls 70 into the anvil cavity 72.

Figure 7:
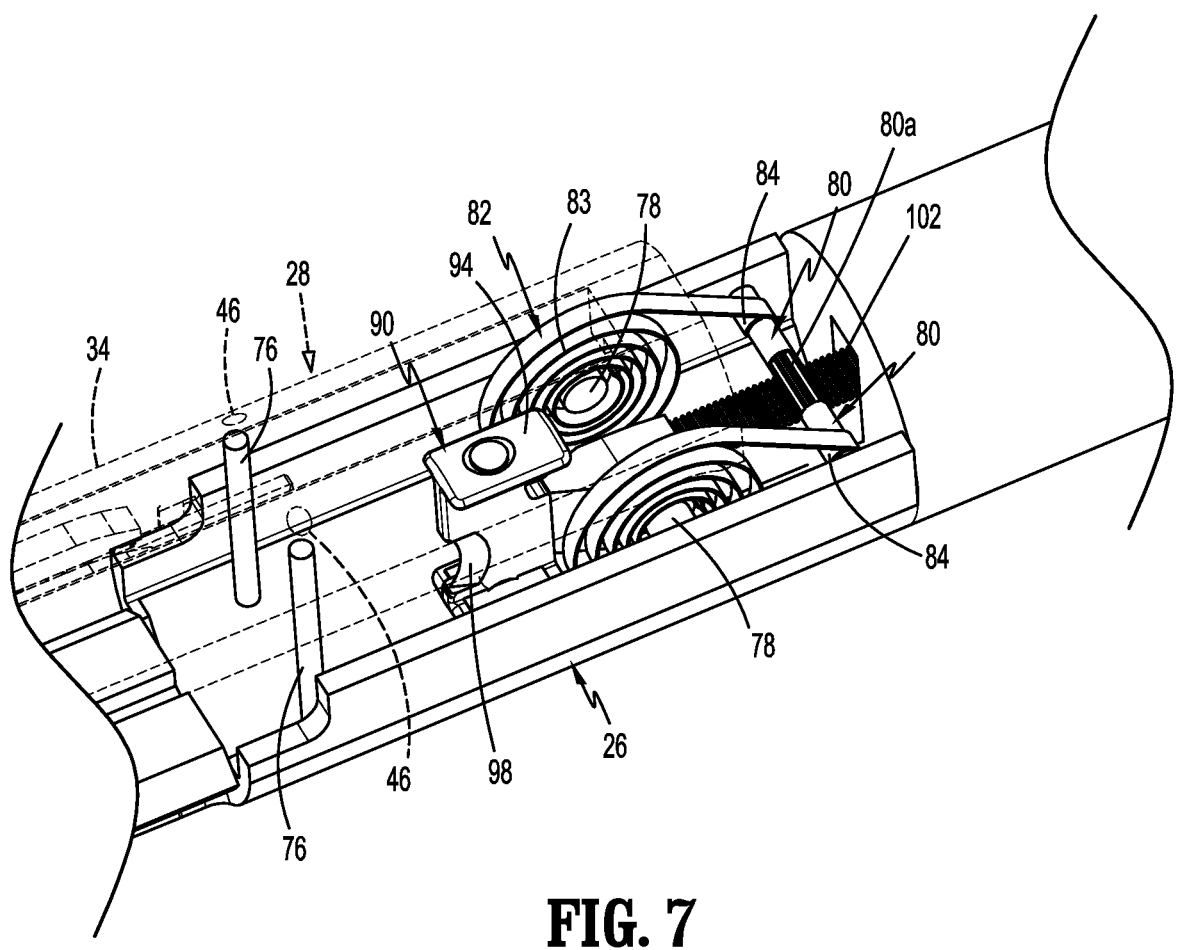
FIG. 7 is a side perspective, cutaway view of a proximal portion of the tool assembly of the surgical stapling device shown in FIG. 1 with a channel of the tool assembly shown in phantom.

FIGS. 3 and 7 illustrate the proximal portion of the tool assembly 16 which includes a biasing mechanism 68. The biasing mechanism 68 includes a roller 80 and a pair of biasing members 82. The roller 80 is rotatably supported between the spaced side walls 70 of the anvil 26 and extends across the anvil cavity 72. The roller 80 has a toothed central portion 80a. In aspects of the disclosure, each of the biasing members 82 includes a spiral spring 82 that has a coil portion 83 and a first end portion 84 that extends from the coil portion 83 and is secured to the roller 80. Each of the spiral springs 82 extends through the circular slot 52 in the channel member 34. The coil portion 83 of each of the spiral springs 82 is supported on one of the bosses 78 of the anvil 26 and sits within one of the circular concavities 48 (FIG. 3) defined in the proximal portions 36a of the side walls 36 of the channel member 34. The outer surfaces of the spiral springs 82 engage inner surfaces of the channel member 34 to urge the cartridge assembly 28 away from the anvil 26 to move the tool assembly 16 to the open position. It is envisioned that the biasing mechanism 68 can have only a single spiral spring 82.

Figure 6:
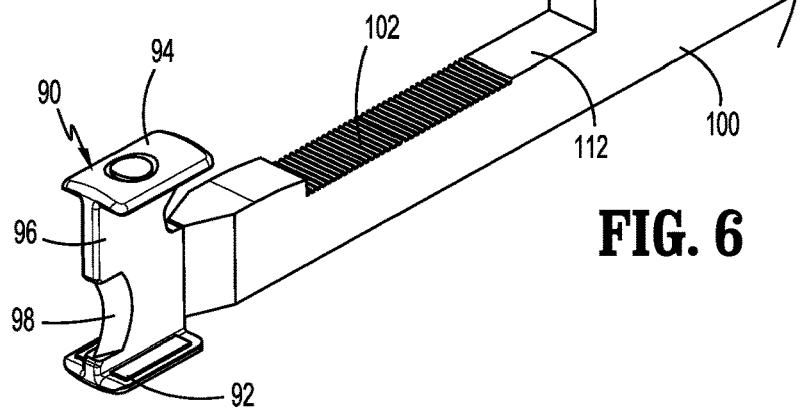
FIG. 6 is a side perspective view of a drive assembly of the tool assembly shown in FIG. 3.

FIGS. 3 and 6 illustrate the drive member 30 which includes an elongate beam 31 having a proximal portion 86 and a distal portion 88. The proximal portion 86 is configured to receive a coupling member (not shown) that couples the drive member 30 to a control rod (not shown) included in the elongate body 14 of the stapling device 10 (FIG. 1). The control rod (not shown) is movable between a retracted position and an advanced position to move the drive member 30 between its retracted and advanced positions. The '139 Patent describes exemplary aspects of a coupling member and a control rod.

The distal portion 88 of the drive member 30 supports a working end 90 that is movable through the anvil 26 and the cartridge assembly 28 to actuate the tool assembly 16. In aspects of the disclosure, the working end 90 of the drive member 30 includes a first beam 92, a second beam 94, and a vertical strut 96 that couples the first beam 92 to the second beam 94. The vertical strut 96 supports a distally facing knife blade 98 and extends through the knife slot 64 of the anvil 26 and the knife slots 42 and 56 of the channel member 34 and the staple cartridge 32. The first beam 92 is received within the internal channel (not shown) of the anvil 26 and the second beam 94 is engaged with the channel member 34 of the cartridge assembly 28 such that movement of the drive member 30 from its retracted position towards its advanced position defines a maximum tissue gap between the staple cartridge 32 and the staple forming surface 66 (FIG. 5) of the anvil 26 as the tool assembly 16 is fired. It is noted that in this aspect of the disclosure, the working end 90 of the drive member 30 does not affect movement of the tool assembly 16 from its open position to its clamped position.

Figure 12:
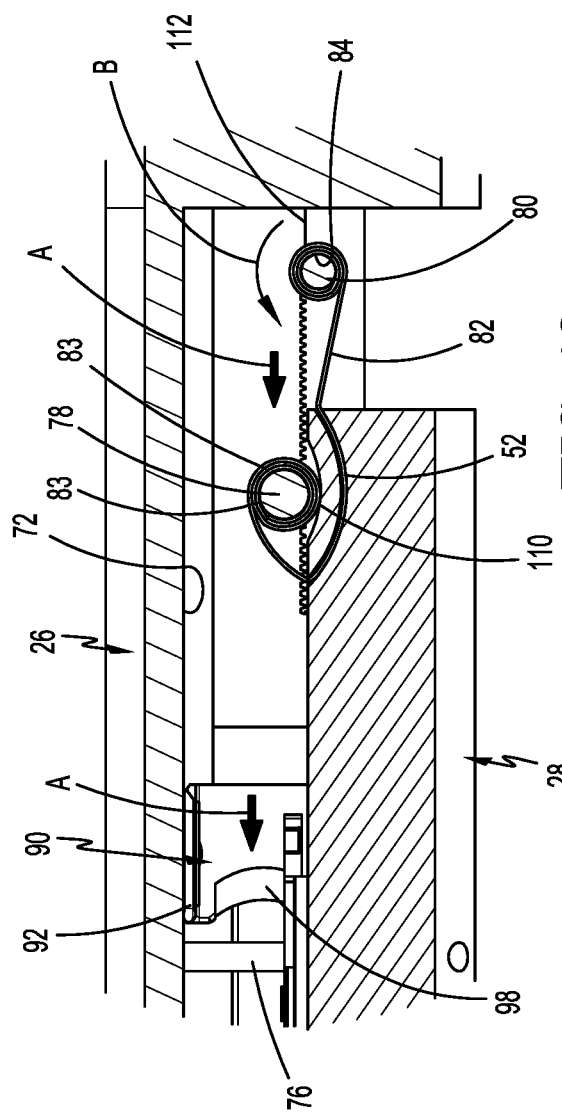
FIG. 12 is an enlarged view of the indicated area of detail shown in FIG. 11.
Figure 15:
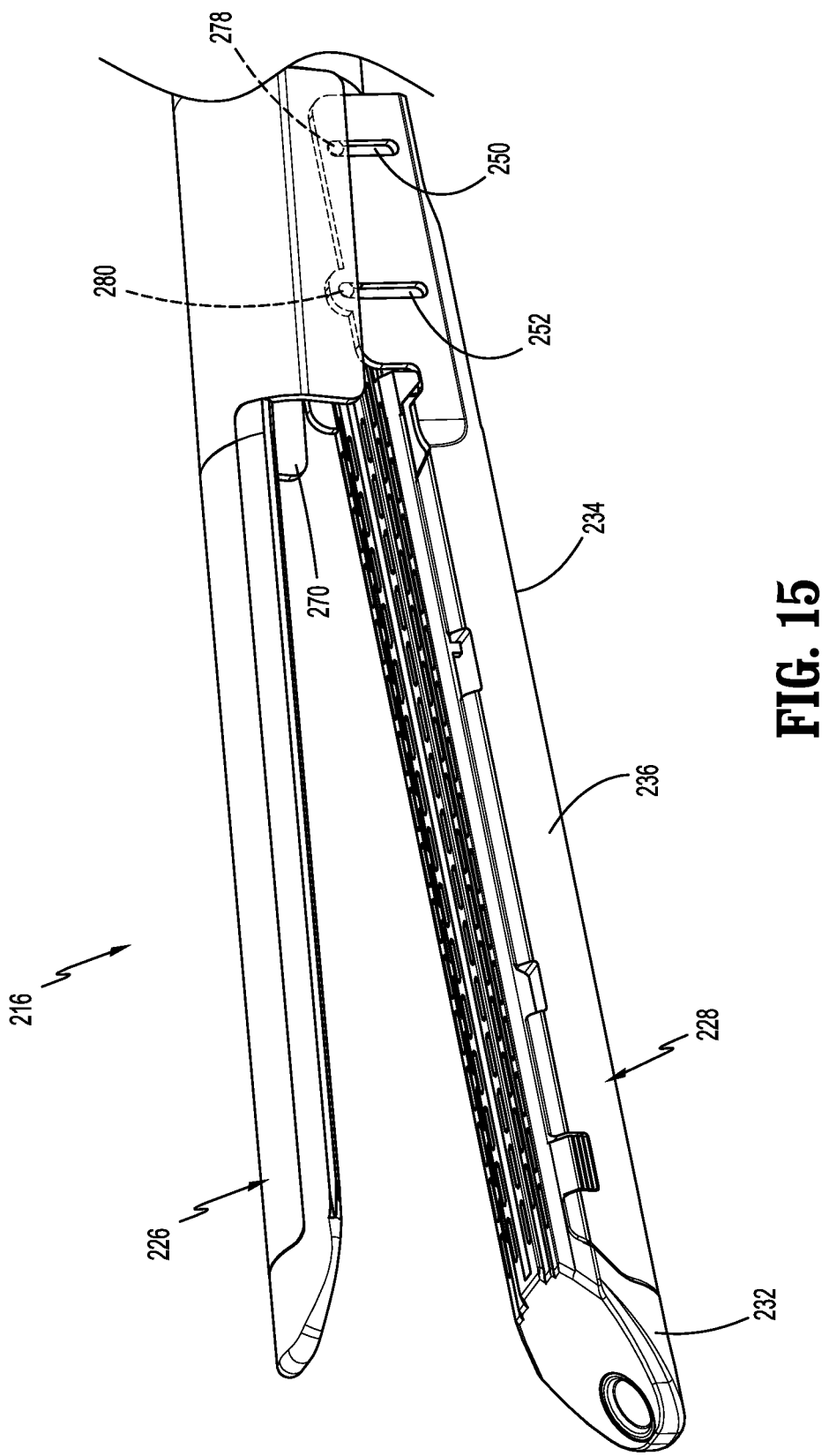
FIG. 15 is an alternative version of the tool assembly of the surgical stapling device shown in FIG. 1.

The elongate beam portion 31 of the drive member 30 includes a toothed rack 102. The toothed rack 102 is engaged with the toothed central portion 80a of the roller 80. When the drive member 30 is moved from its retracted position to its advanced position, engagement between the toothed central portion 80a of the roller 80 and the toothed rack 102 of the drive member 30 causes the roller 80 to rotate within the anvil cavity 72. Rotation of the roller 80 winds the spiral springs 82 about the roller 80 to move the coil portions 83 of the spiral springs 82 from an expanded condition (FIG. 8) to a contracted or condition (FIG. 12). When the spiral springs 82 are in their expanded condition, the coil portions 83 of the spiral springs 82 are positioned between the anvil 26 and the channel member 30 of the cartridge assembly 28 and urge the cartridge assembly 28 away from the anvil 26 to move the tool assembly 16 to the open position. When the spiral springs 82 are in their contracted condition, the coil portions 83 of the spiral springs 82 are contracted about the bosses 78 of the anvil 26 and the spiral springs 82 which extend through the slots 52 in the channel member 34 pulls the cartridge assembly 28 towards the anvil 26 such that the tool assembly 16 moves from its open position to its clamped position.

FIGS. 8-10 illustrate the tool assembly 16 in the open position. In the open position of the tool assembly 16, the drive member 30 is in a retracted position with the toothed rack 102 on the beam portion 100 of the drive member 30 engaged with the toothed central portion 80a of the roller 80. When the drive member 30 is in the retracted position, the spiral springs 82 are in their expanded position such that the coil portions 83 of the spiral springs 82 urge the cartridge assembly 28 away from the anvil 26 to move the tool assembly 16 to the open position. The pins 76 of the anvil 26 are received within the bores 46 of the channel member 34 to maintain the anvil 26 in parallel alignment with the staple cartridge 32 of the cartridge assembly 28.

FIGS. 11-14 illustrate the tool assembly 16 in the clamped position. When the drive member 30 is moved from its retracted position towards its advanced position in the direction indicated by arrows "A" in FIGS. 11 and 12, engagement between the toothed rack 102 of the beam portion 100 of the drive member 30 and the roller 80 causes the roller 80 to rotate in the direction indicated by arrow "B" in FIG. 12 within the anvil cavity 72 of the anvil 26. As described above, the first end 84 of the spiral spring 82 is secured to the roller 80. Thus, as the roller 80 rotates within the anvil cavity 72, the first end 84 of the spiral spring 82 is wound about the roller 82 to contract the coil portions 83 of the spiral springs 82 about the bosses 78. As the spiral springs 82 are wound about the roller 80, the spiral springs 82 which extend through the circular slots 52 of the channel member 34 pulls the cartridge assembly 28 toward the anvil 26 in the direction indicated by arrow "C" in FIG. 11 to move the tool assembly 16 to the clamped position. As described above, the pins 76 move through the bores 46 in the channel member 34 to maintain the anvil 26 and the cartridge assembly 28 in parallel alignment as the cartridge assembly 28 moves towards the anvil 26. In the clamped position of the tool assembly 16, the staple forming surface 66 of the anvil 26 is in juxtaposed alignment with the staple cartridge 28.

It is envisioned that the cartridge assembly 28 could be fixedly secured to the elongate body 14 (FIG. 1) and the anvil 26 could be movable in relation to the elongate body 14 toward the cartridge assembly 28.

It is noted that the beam portion 100 of the drive member 30 immediately proximal of the toothed rack 100 includes a flat surface 112 (FIG. 6). After the tool assembly 16 is in the clamped position, the drive member 30 continues to move towards its advanced position to actuate the tool assembly 16. The flat surface 112 allows the beam portion 100 to pass over the roller 80 without rotating the roller 80.

Figure 16:
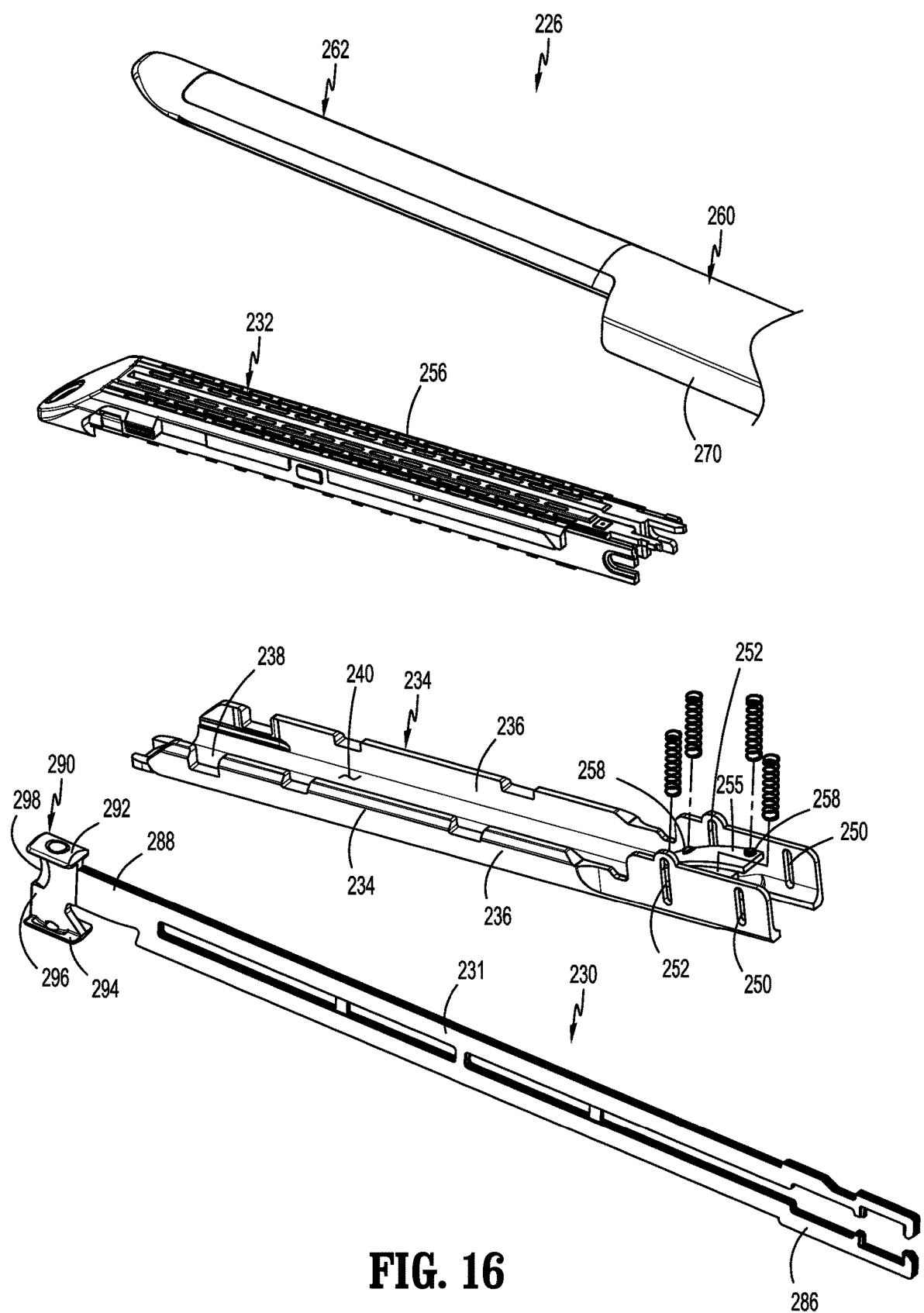
FIG. 16 is a side perspective exploded view of the tool assembly shown in FIG. 15.
Figure 17:
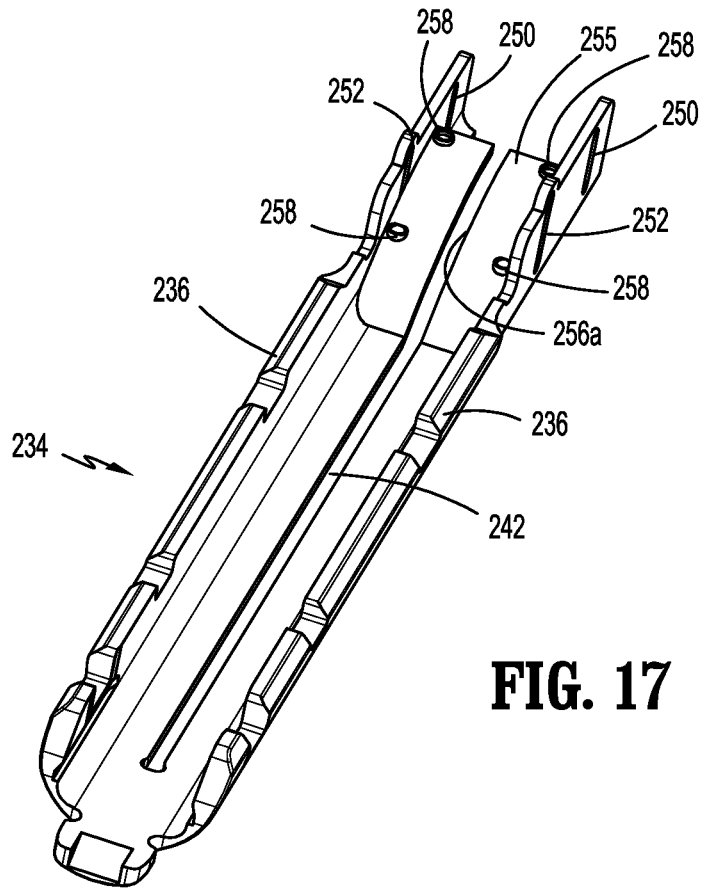
FIG. 17 is a perspective view from above of the channel of the tool assembly shown in FIG. 16.

FIGS. 15-26 illustrate an alternate version of the tool assembly of the stapling device 10 (FIG. 1) shown generally as tool assembly 216. The tool assembly 216 is like tool assembly 16 (FIG. 3) and includes an anvil 226, a cartridge assembly 228, and a drive member 230 (FIG. 16). The anvil 226 is fixedly secured to a distal end of the proximal body portion 18a (FIG. 1) of the reload assembly 18 (or to the distal end of the elongate body 14) (FIG. 1). The cartridge assembly 228 is supported on the anvil 226 for movement between an open position (FIG. 15) and a clamped position (FIG. 25) and includes a staple cartridge 232 and a channel member 234. The channel member 234 includes side walls 236 and a base wall 238 that define a channel cavity 240 (FIG. 16) that receives the staple cartridge 232. The base wall 238 of the channel member 234 defines a knife slot 242 (FIG. 17) that extends through the channel member 234 along most of its length and includes a closed distal end. The knife slot 242 receives a portion of the drive member 230 to facilitate movement of the drive member 230 in relation to the anvil 226 and cartridge assembly 228 between retracted and advanced positions as described below.

Figure 18:
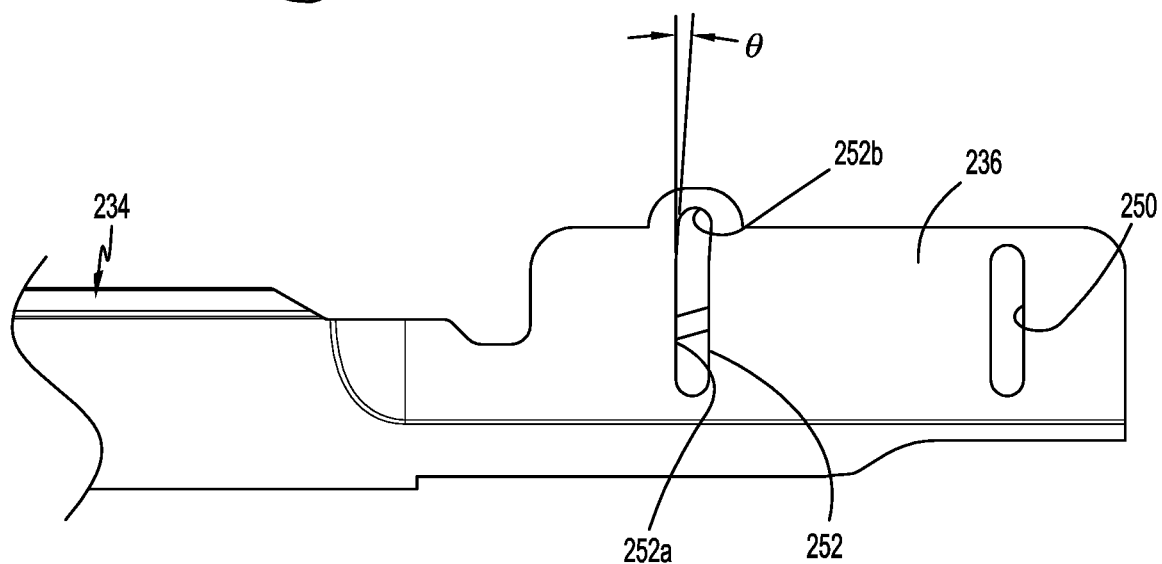
FIG. 18 is a side view of a proximal portion of the channel shown in FIG. 17.

FIGS. 15-18 illustrate the channel member 234 which includes a proximal portion that is defined by the side walls 236 of the channel member 234. The proximal portion of each of the side walls 236 defines first and second slots 250 and 252 (FIG. 18). The slots 252 are substantially linear and vertically oriented as viewed in FIG. 18. The slots 252 are also vertically oriented and include a linear portion 252a and an angled portion 252b. The angled portion 252b of each of the slots 252 defines an angle θ with the axis of the linear portion. The angle θ is selected to allow the channel member 234 to pivot in relation to the anvil 226 from a pivoted position (FIG. 21) to a position in parallel alignment with the anvil 26 (FIG. 23) and can be from about 1 degree to about 5 degrees. In some aspects of the disclosure, angle θ is about 3 degrees.

The channel member 234 includes a ramp 255 that is supported between the proximal portion of the side walls 236. The ramp 255 defines a knife slot 255a that is aligned with the knife slot 242 (FIG. 17) of the channel member 234 and supports a pair of spring mounts 258 which are positioned on each side of the knife slot 256a.

The staple cartridge 232 is received within the channel cavity 240 of the channel member 234 and includes a cartridge body 254 that defines a central knife slot 256 and rows of staple pockets 257 on each side of the central knife slot 256. It is envisioned that two or more rows of staple pockets 257 can be provided on each side of the central knife slot 256. It is also envisioned that the staple pockets 257 need not be aligned in rows but rather a variety of different arrays of staple pockets 257 can be defined on each side of the central knife slot 256. Each of the staple pockets 257 receives a staple and a pusher (not shown). For a more detailed description of an exemplary staple cartridge 232 including staples and pushers, see the '139 Patent.

FIGS. 16 and 19 illustrate the anvil 226 which includes a proximal portion 260 and a distal portion 262. The distal portion 262 of the anvil 226 defines a central knife slot 264 and includes a staple forming surface 266. The central knife slot 264 extends through the staple forming surface 266 and communicates with an internal channel (not shown) defined within the anvil 226. The central knife slot 264 and the internal channel (not shown) within the anvil 226 receive a portion of the drive member 230 as the drive member 30 is moved between its retracted and advanced positions as described in further detail below.

The proximal portion 260 of the anvil 226 includes a pair of spaced side walls 270 that defines an anvil cavity 272 that receives the proximal portion of the channel member 234. The anvil cavity 272 is defined in part by a base wall 274 of the anvil 226. The base wall 274 defines a continuation of the central knife slot 264 such that the central knife slot 264 extends through a proximal end of the base wall 274. The base wall 274 includes spring mounts 276 (FIG. 19). The side walls 270 support pivot members 278 and 280 that extend from the side walls 270 inwardly into the anvil cavity 272. The pivot members 280 are positioned distally of the pivot members 278 and are received within the first slots 250 of the channel member 234. The pivot members 280 are received within the second slots 252 of the channel member.

FIG. 16 illustrates the drive member 230 which includes an elongate beam portion 231 including a proximal portion 286 and a distal portion 288. The proximal portion 286 is configured to receive a coupling member (not shown) that couples the drive member 230 to a control rod (not shown) included in the elongate body 14 of the stapling device 10 (FIG. 1). The control rod (not shown) is movable between a retracted position and an advanced position to move the drive member 230 between its retracted and advanced positions. The '139 Patent describes exemplary aspects of a coupling member and a control rod. The distal portion 288 of the elongate beam 231 supports a working end 290 that is movable through the anvil 226 and the cartridge assembly 228 to actuate the tool assembly 216. In aspects of the disclosure, the working end 290 of the drive member 230 includes a first beam 292, a second beam 294, and a vertical strut 296 that couples the first beam 292 to the second beam 294. The vertical strut 296 supports a distally facing knife blade 298 and extends through the knife slot 264 (FIG. 19) of the anvil 226 and the knife slots 242 (FIG. 17) and 256 of the channel member 234 and the staple cartridge 232, respectively. The first beam 292 is received within the internal channel (not shown) of the anvil 226 and the second beam 294 is engaged with the channel member 234 of the cartridge assembly 228 such that movement of the drive member 230 from its retracted position towards its advanced position moves the cartridge assembly 228 towards the anvil 226 to move the tool assembly 216 to the clamped position (FIG. 25) and define a maximum tissue gap between the staple cartridge 232 and the staple forming surface 266 (FIG. 5) of the anvil 226 as the tool assembly 216 is fired.

FIGS. 16 and 20 illustrate the biasing members 300 of the tool assembly 16. In aspects of the disclosure, the biasing members 300 include coil springs, e.g., 4, that are positioned between the proximal portions of the anvil 226 and the channel member 228. The coil springs 300 have a first end secured to the spring mounts 258 on the channel member 234 and a second end secured to the spring mounts 276 on the base wall 274 of the anvil 226. The coil springs 300 urge the proximal portions of the anvil 226 and channel member 234 of the cartridge assembly 228 apart to move the tool assembly 216 to its open position.

Figure 21:
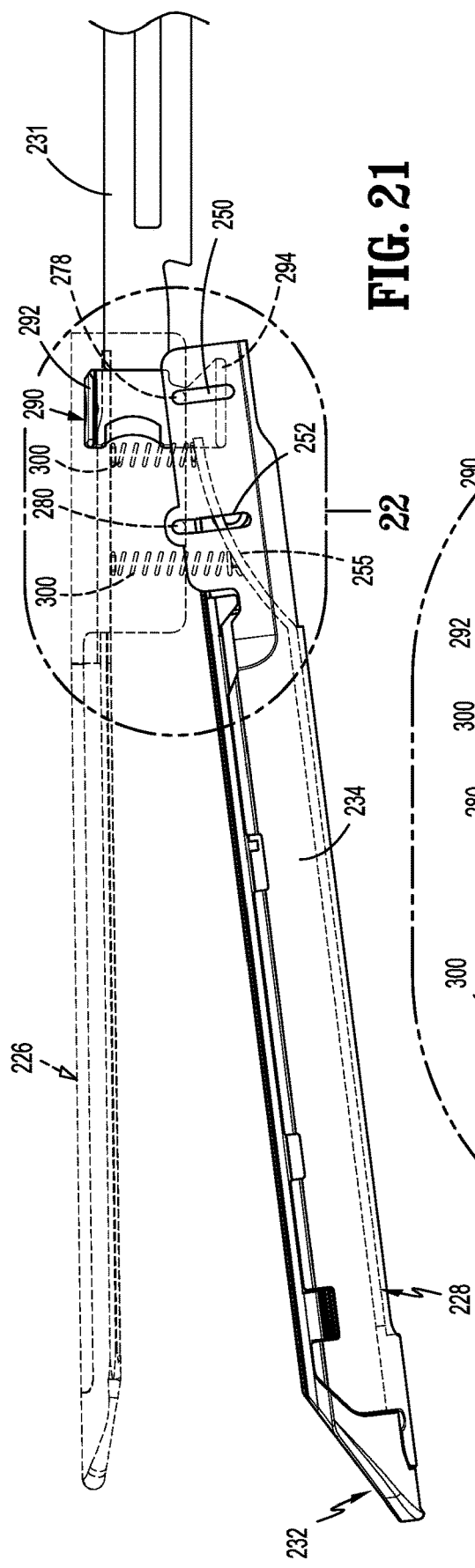
FIG. 21 is a side perspective view of the tool assembly shown in FIG. 15 in the open position with the anvil shown in phantom.
Figure 22:
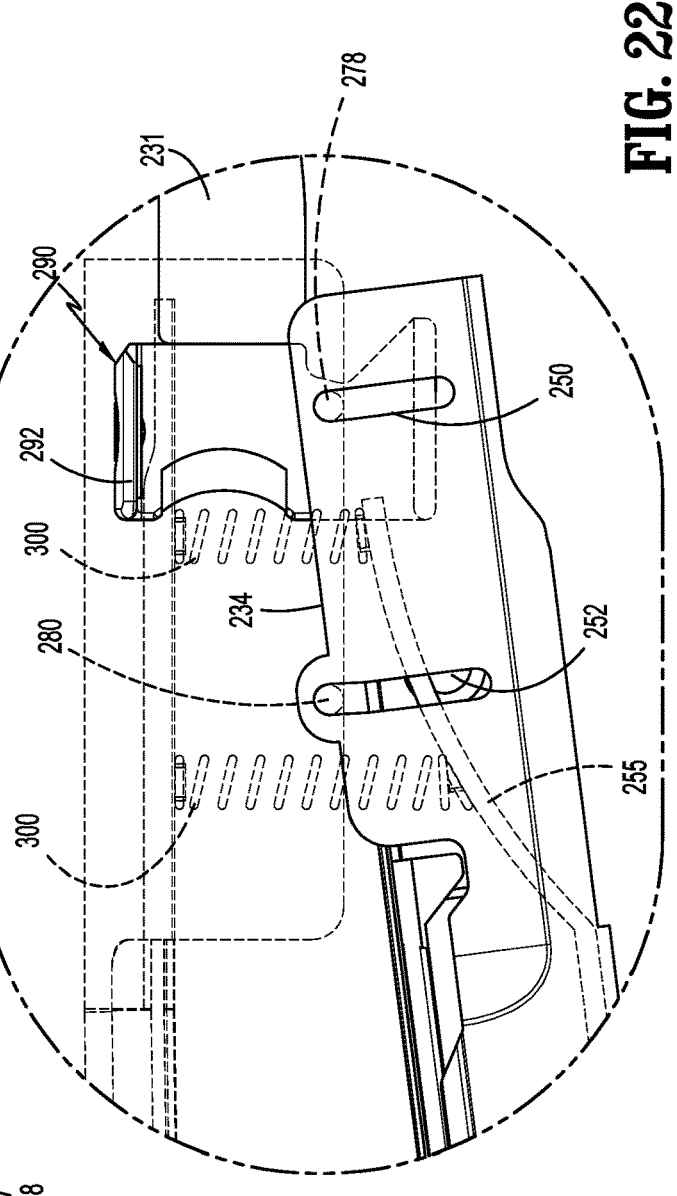
FIG. 22 is an enlarged view of the indicated area of detail shown in FIG. 21.

FIGS. 21 and 22 illustrate the tool assembly 216 in the open position. In the open position, the drive member 230 is in its retracted position with the working end 290 of the drive member 230 positioned proximally of the ramp 255, and the pivot members 278 and 280 are positioned within upper ends of the slots 250 and 252 of the channel member 234. The coil springs 300 which are engaged with the proximal portions of the anvil 226 and cartridge assembly 228 urge the proximal portions of the anvil 226 and the cartridge assembly 228 apart to move the tool assembly 216 to the open position.

FIGS. 23 and 24 illustrate the tool assembly 216 as the tool assembly 216 is moved from the open position towards the clamped position. When the drive member 230 is moved from its retracted position towards its advanced position in the direction indicated by arrows "E" in FIG. 23, the second beam 294 of the working end 290 of the drive member 230 engages and moves along an underside of the ramp 255 and pivots the cartridge assembly 228 about the pivot member 278 in the direction of arrow "F" in FIG. 23 towards the anvil 226 to an intermediate position in which the cartridge assembly 228 is in parallel alignment with the anvil 226. As the cartridge assembly 228 pivots to the intermediate position, the pivot members 280 move within the angled portions 252b of the second slots 252 towards the linear portions 252a of the slots 252.

FIGS. 25 and 26 illustrate the tool assembly 216 as the tool assembly 216 is moved from the intermediate position towards the clamped position. When the drive member 230 is moved from the position shown in FIG. 23 towards its advanced position in the direction indicated by arrows "E" in FIG. 25, the second beam 294 of the working end 290 of the drive member 230 continues to engage and move along the underside of the ramp 255 to urge the cartridge assembly 228 in the direction of arrows "G" in FIG. 25 towards the anvil 226 and towards the clamped position in which the cartridge assembly 228 is in juxtaposed parallel alignment with the anvil 226. As the cartridge assembly 228 moves to the clamped position, the pivot members 280 move within the linear portions 252a of the slots 252 and the pivot members 278 move within the linear slots 250 to maintain the anvil 226 and the cartridge assembly 228 in substantially parallel alignment.

Although not shown, continued movement of the drive member 230 in relation to the anvil 226 and the cartridge assembly 228 towards its advanced position fires staples from the staple cartridge 232 of the cartridge assembly 228 into the gap defined between the staple forming surface 266 of the anvil 226 and the staple cartridge 232 of the cartridge assembly 228 and into the staple forming surface 266 of the anvil assembly 226. For a more detailed description of the operation and firing of an exemplary tool assembly, see the '139 Patent.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure.

Accordingly, the disclosure is not to be limited by what has been particularly shown and described, except as indicated by the appended claims.

What is claimed is:

1. A tool assembly comprising:
an anvil including a body having a proximal portion and a distal portion, the body defining a central knife slot and including a staple forming surface, the proximal portion of the body including spaced side walls defining an anvil cavity, each of the side walls supporting a distal pivot member and a proximal pivot member, the distal pivot member longitudinally spaced from the proximal pivot member, the distal and proximal pivot members extending from the respective side walls of the channel member into the anvil cavity;
a cartridge assembly defining a longitudinal axis and including a channel member and a staple cartridge, the channel member including side walls and a base wall that define a channel cavity that receives the staple cartridge, each of the side walls of the channel member having a proximal portion that defines first and second slots, the first and second slots defining axes that are substantially perpendicular to the longitudinal axis of the cartridge assembly, the first slots being longitudinally spaced from the second slots, each of the first slots receiving a respective one of the distal pivot members, and each of the second slots receiving a respective one of the proximal pivot members, the cartridge assembly movable in relation to the anvil to move the tool assembly from an open position to a clamped position; and
a drive member including a beam portion and a working end, the drive member movable in relation to the anvil and the cartridge assembly from a retracted position to an intermediate position and subsequently to a clamped position to move the cartridge assembly in relation to the anvil from the open position to the clamped position, wherein the first and second slots are configured such that movement of the drive member from the retracted position to the intermediate position pivots the cartridge assembly in relation to the anvil into parallel alignment with the anvil and movement of the drive member from its intermediate position to its clamped position moves the cartridge assembly in relation to the anvil to the clamped position while maintaining the cartridge assembly in parallel relation to the anvil.

2. The tool assembly of claim 1, wherein the first slots include an angled portion that allows the cartridge assembly to pivot in relation to the anvil as the drive member moves from its retracted position towards the intermediate position.

3. The tool assembly of claim 2, further including biasing members supported between the proximal portion of the anvil and the proximal portion of the channel member, the biasing members urging the cartridge assembly in relation to the anvil towards its open position.

4. The tool assembly of claim 3, wherein the channel member supports a ramp, and the working end of the drive member includes a first beam, a second beam, and a vertical strut interconnecting the first and second beams, the first beam engaging the anvil and the second beam engaging the ramp of the cartridge assembly as the drive member is moved from its retracted position to its clamped position to move the cartridge assembly in relation to the anvil from its open position to its clamped position.

5. The tool assembly of claim 4, wherein the biasing members include coil springs that are supported between the ramp of the cartridge assembly and the anvil.

6. The tool assembly of claim 5, wherein the ramp supports spring mounts that secure the coil springs to the ramp.

7. The tool assembly of claim 6, wherein the channel member defines a central knife slot, and the ramp supports two spring mounts on each side of the central knife slot of the channel member.

8. The tool assembly of claim 7, wherein the two spring mounts on each side of the central knife slot of the channel member are longitudinally spaced from each other.

9. The tool assembly of claim 8, wherein the biasing members include four biasing members, one of the biasing members secured to each of the spring mounts on the ramp.

10. A surgical stapling device comprising:
a handle assembly including a stationary handle;
an elongate body having a proximal portion and a distal portion, the proximal portion coupled to the handle assembly; and
a tool assembly supported on the distal portion of the elongate body, the tool assembly including:
an anvil including a body having a proximal portion and a distal portion, the body defining a central knife slot and including a staple forming surface, the proximal portion of the body including spaced side walls defining an anvil cavity, each of the side walls supporting a distal pivot member and a proximal pivot member, the distal pivot member longitudinally spaced from the proximal pivot member, the distal and proximal pivot members extending from the respective side walls of the channel member into the anvil cavity;
a cartridge assembly defining a longitudinal axis and including a channel member and a staple cartridge, the channel member including side walls and a base wall that define a channel cavity that receives the staple cartridge, each of the side walls of the channel member having a proximal portion that defines first and second slots, the first and second slots defining axes that are substantially perpendicular to the longitudinal axis of the cartridge assembly, the first slots being longitudinally spaced from the second slots, each of the first slots receiving a respective one of the distal pivot members, and each of the second slots receiving a respective one of the proximal pivot members, the cartridge assembly movable in relation to the anvil to move the tool assembly from the open position to the clamped position; and
a drive member including a beam portion and a working end, the drive member movable in relation to the anvil and the cartridge assembly from a retracted position to an intermediate position and subsequently to a clamped position to move the cartridge assembly in relation to the anvil from the open position to the clamped position, wherein the first and second slots are configured such that movement of the drive member from the retracted position to the intermediate position pivots the cartridge assembly in relation to the anvil into parallel alignment with the anvil and movement of the drive member from its intermediate position to its clamped position moves the cartridge assembly in relation to the anvil to the clamped position while maintaining the cartridge assembly in parallel relation to the anvil.

11. The surgical stapling device of claim 10, wherein the first slots include an angled portion that allows the cartridge assembly to pivot in relation to the anvil as the drive member moves from its retracted position towards the intermediate position.

12. The surgical stapling device of claim 11, further including biasing members supported between the proximal portion of the anvil and the proximal portion of the channel member, the biasing members urging the cartridge assembly in relation to the anvil towards its open position.

13. The surgical stapling device of claim 12, wherein the channel member supports a ramp, and the working end of the drive member includes a first beam, a second beam, and a vertical strut interconnecting the first and second beams, the first beam engaging the anvil and the second beam engaging the ramp of the cartridge assembly as the drive member is moved from its retracted position to its clamped position to move the cartridge assembly in relation to the anvil from its open position to its clamped position.

14. The surgical stapling device of claim 13, wherein the biasing members include coil springs that are supported between the ramp of the cartridge assembly and the anvil.

15. The surgical stapling device of claim 14, wherein the ramp supports spring mounts that secure the coil springs to the ramp.

16. The surgical stapling device of claim 15, wherein the channel member defines a central knife slot, and two of the spring mounts are supported on the ramp on each side of the central knife slot of the channel member.

17. The surgical stapling device of claim 16, wherein the two spring mounts on each side of the central knife slot of the channel member are longitudinally spaced from each other.

18. The surgical stapling device of claim 17, wherein the biasing members include four biasing members, one of the biasing members secured to each of the spring mounts on the ramp.

19. A tool assembly comprising:
an anvil including a body having a proximal portion and a distal portion, the body defining a central knife slot and including a staple forming surface, the proximal portion of the body including spaced side walls defining an anvil cavity, each of the side walls supporting a distal pivot member and a proximal pivot member, the distal pivot member longitudinally spaced from the proximal pivot member, the distal and proximal pivot members extending from the respective side walls of the body of the anvil into the anvil cavity;
a cartridge assembly defining a longitudinal axis and including a channel member and a staple cartridge, the channel member including side walls and a base wall that define a channel cavity that receives the staple cartridge, each of the side walls of the channel member having a proximal portion that defines first and second slots, the first and second slots defining axes that are substantially perpendicular to the longitudinal axis of the cartridge assembly, the first slots being longitudinally spaced from the second slots, each of the first slots receiving a respective one of the distal pivot members, and each of the second slots receiving a respective one of the proximal pivot members, the cartridge assembly movable in relation to the anvil to move the tool assembly from an open position to a clamped position; and
biasing members supported between the proximal portion of the anvil and the proximal portion of the channel member, the biasing members urging the cartridge assembly in relation to the anvil towards the open position.

20. The tool assembly of claim 19, wherein the channel member includes a ramp that is positioned between the side walls of the channel member in the proximal portion of the channel member, the biasing members including coil springs that are supported between the ramp of the cartridge assembly and the anvil.

* * * * *